(12) United States Patent
Libbus et al.

(10) Patent No.: US 10,898,714 B2
(45) Date of Patent: Jan. 26, 2021

(54) STIMULATION SUSPENSION IN RESPONSE TO PATIENT DISCOMFORT OR STATE

(71) Applicant: CYBERONICS, INC., Houston, TX (US)

(72) Inventors: Imad Libbus, St. Paul, MN (US); Scott R. Stubbs, Maple Grove, MN (US); Bruce H. Kenknight, Maple Grove, MN (US)

(73) Assignee: LivaNova USA, Inc., Houston, TX (US)

( * ) Notice: Subject to any disclaimer, the term of this patent is extended or adjusted under 35 U.S.C. 154(b) by 486 days.

(21) Appl. No.: 15/285,337

(22) Filed: Oct. 4, 2016

(65) Prior Publication Data

US 2017/0095669 A1     Apr. 6, 2017

Related U.S. Application Data

(60) Provisional application No. 62/237,078, filed on Oct. 5, 2015.

(51) Int. Cl.
*A61N 1/36*     (2006.01)
*A61B 5/08*     (2006.01)
*A61B 5/113*     (2006.01)

(52) U.S. Cl.
CPC ....... *A61N 1/36053* (2013.01); *A61N 1/3614* (2017.08); *A61N 1/36114* (2013.01); *A61N 1/36132* (2013.01); *A61N 1/36139* (2013.01); *A61N 1/36167* (2013.01); *A61B 5/0809* (2013.01); *A61B 5/0823* (2013.01); *A61B 5/1135* (2013.01)

(58) Field of Classification Search
CPC .. A61N 1/36071; A61N 1/36125; A61N 1/05; A61N 1/08; A61N 1/36021; A61N 1/37; A61N 1/00; A61N 1/36; A61N 1/36146; A61N 1/36585; A61N 1/3702; A61B 5/042; A61B 5/7275; A61B 5/0004; A61B 5/04; A61B 5/7264; G06F 19/345
See application file for complete search history.

(56) References Cited

U.S. PATENT DOCUMENTS 7,177,680 B2 *    2/2007    Sharma ................ A61N 1/0573
                                                                                                    606/32
8,571,654 B2    10/2013    Libbus et al.
8,600,505 B2    12/2013    Libbus et al.
(Continued)

OTHER PUBLICATIONS

International Search Report and Written opinion for PCT Patent Application No. PCT/US2016/055366, dated Mar. 10, 2017, 21 pages.

(Continued)

*Primary Examiner* — Deborah L Malamud
(74) *Attorney, Agent, or Firm* — Foley & Lardner LLP

(57) ABSTRACT

Systems and methods are provided for delivering neurostimulation therapies to patients. Stimulation from an implantable medical device (IMD) may be suspended in response to detecting a patient discomfort event, such as a cough, throat irritation, or voice alteration. The suspension period may be based on at least one of a severity level of the patient discomfort event and a patient physical state, such as being asleep or lying down. Detection of a patient discomfort event may be calibrated.

18 Claims, 10 Drawing Sheets

(56) References Cited

U.S. PATENT DOCUMENTS

| | | |
|---|---|---|
| 8,688,212 B2* | 4/2014 | Libbus ................ A61B 5/0464 607/17 |
| 2008/0051839 A1 | 2/2008 | Libbus et al. |
| 2008/0058892 A1 | 3/2008 | Haefner et al. |
| 2011/0282416 A1 | 11/2011 | Hamann et al. |
| 2012/0330373 A1 | 12/2012 | Ternes et al. |
| 2013/0158616 A1 | 6/2013 | Libbus et al. |
| 2013/0245722 A1 | 9/2013 | Ternes et al. |
| 2014/0135864 A1 | 5/2014 | Libbus et al. |
| 2014/0277256 A1 | 9/2014 | Osorio |
| 2015/0273214 A1 | 10/2015 | Kenknight et al. |

OTHER PUBLICATIONS

De Ferrari et al., Chronic Vagus Nerve Stimulation: A New and Promising Therapeutic Approach for Chronic Heart Failure, European Heart Journal, vol. 32, Oct. 28, 2010, pp. 847-855.

Hellyer, et al., "Autonomic Nerve Activity and Blood Pressure in Ambulatory Dogs," Heart Rhythm, vol. 11(2), Feb. 2014, pp. 307-313.

Zhang et al., Chronic Vagus Nerve Stimulation Improves Autonomic Control and Attenuates Systemic Inflammation and Heart Failure Progression in a Canine High-Rate Pacing Model, Circulation Heart Fail 2009, vol. 2, Sep. 22, 2009, pp. 692-699.

First Report on Examination for EP Application No. 16781647.9 dated Aug. 13, 2020, 5 pages.

* cited by examiner

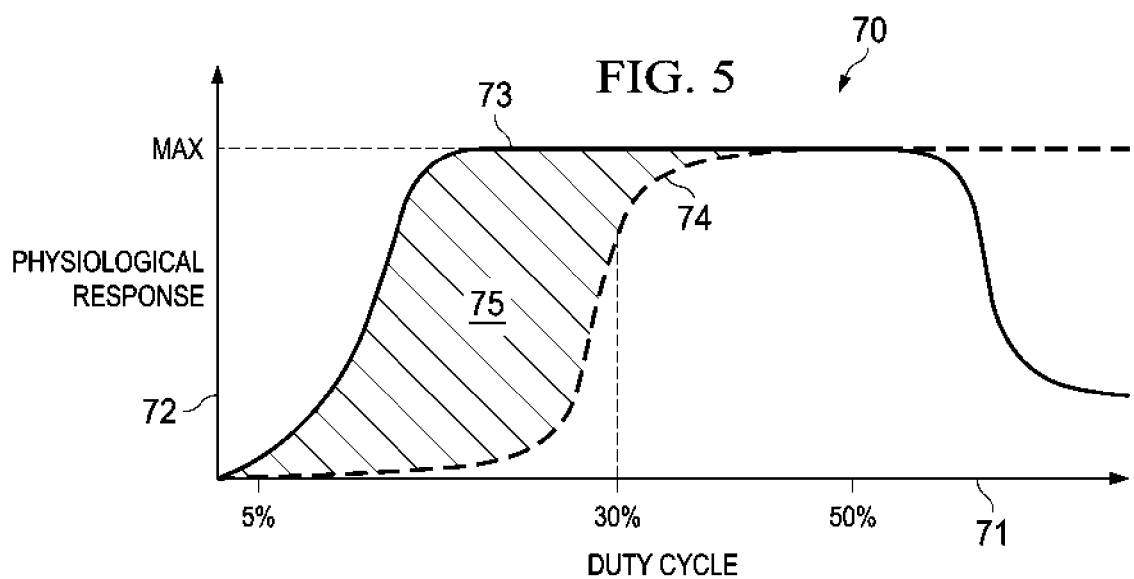
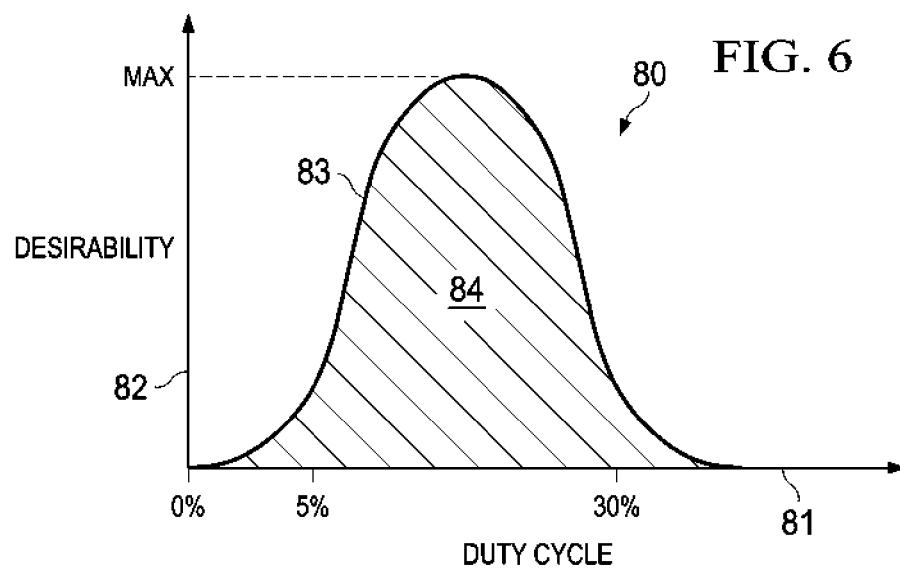
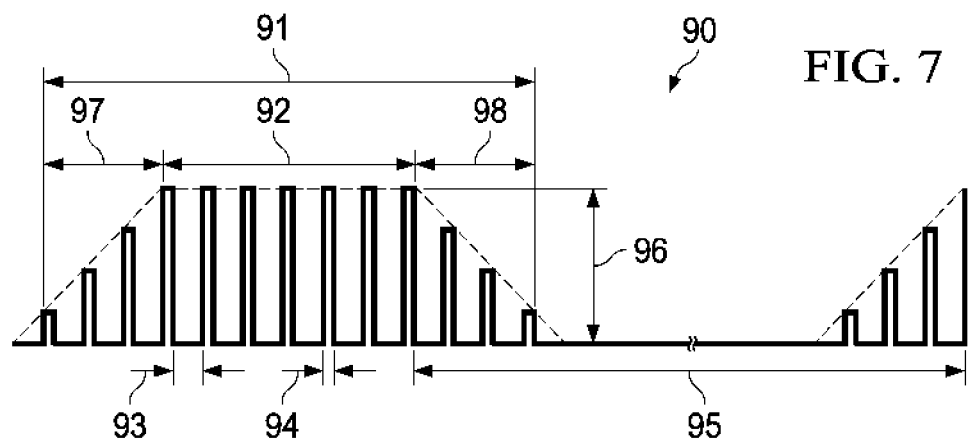

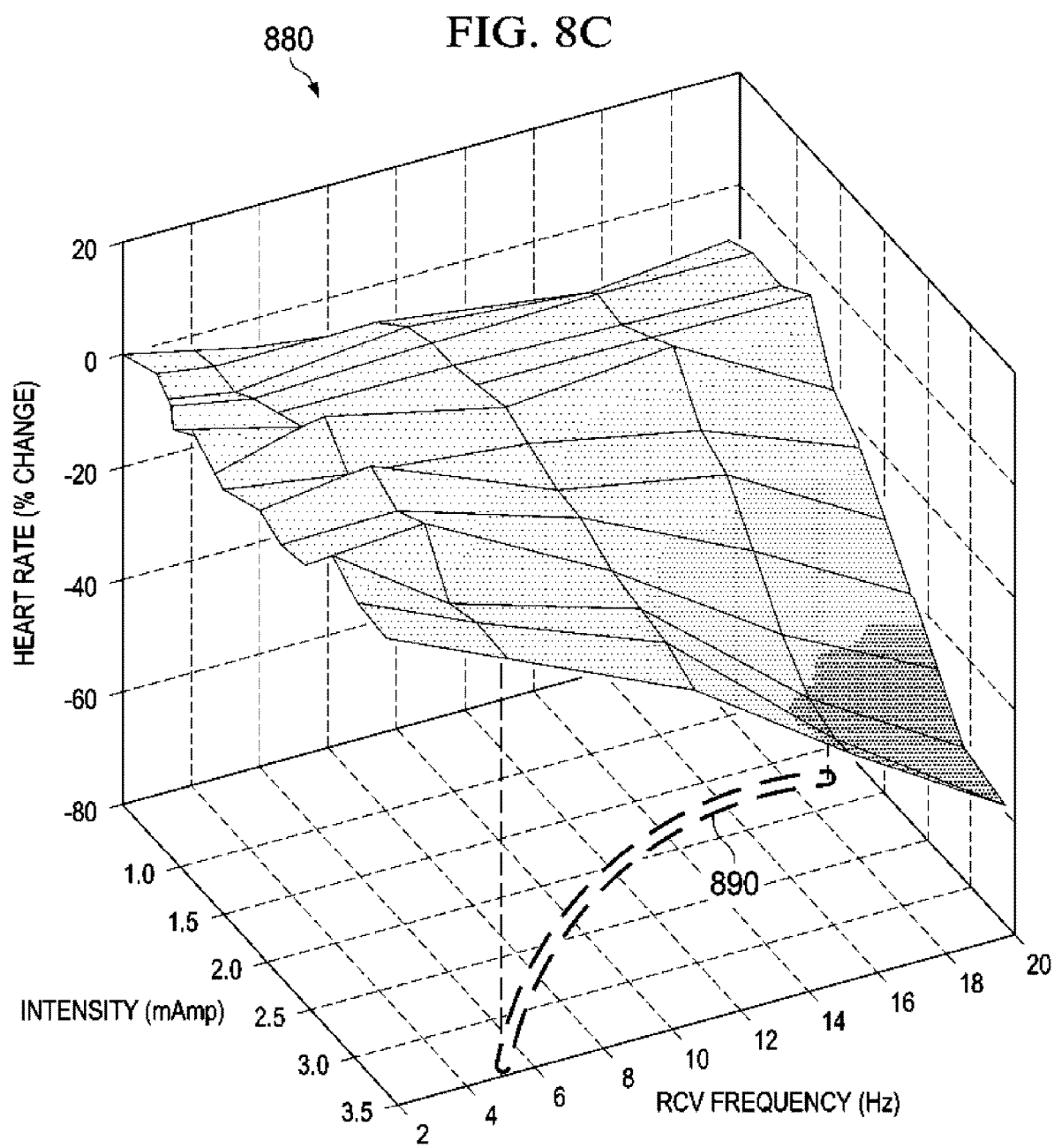

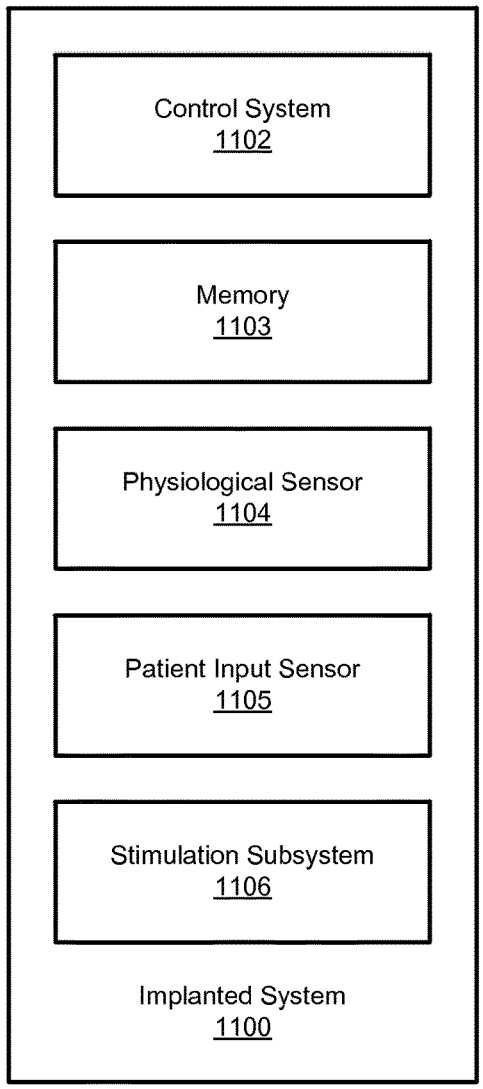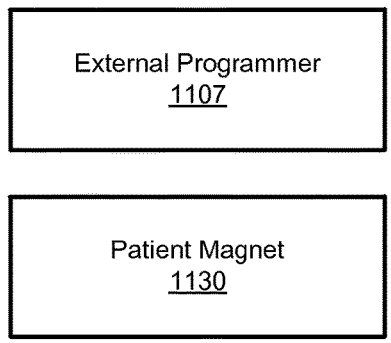
FIG. 11A
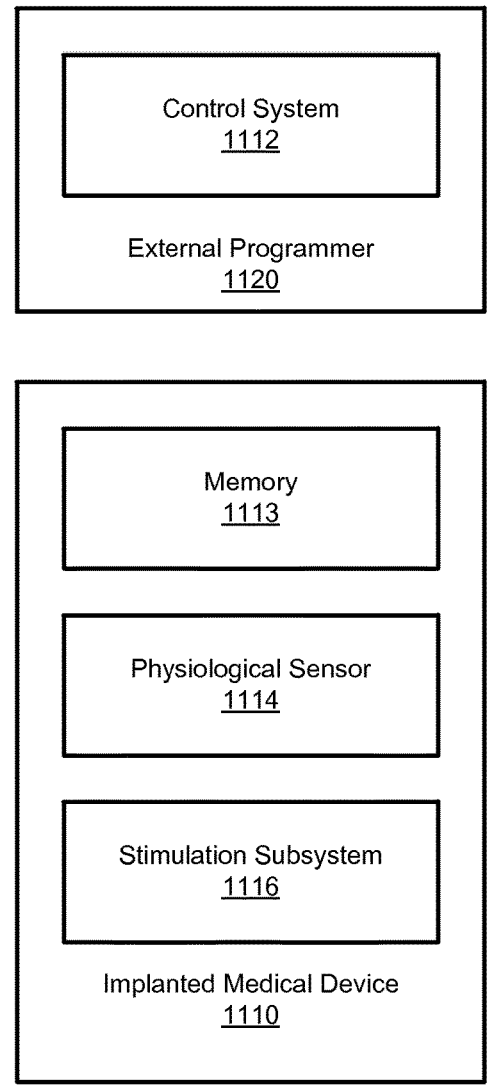
FIG. 11B

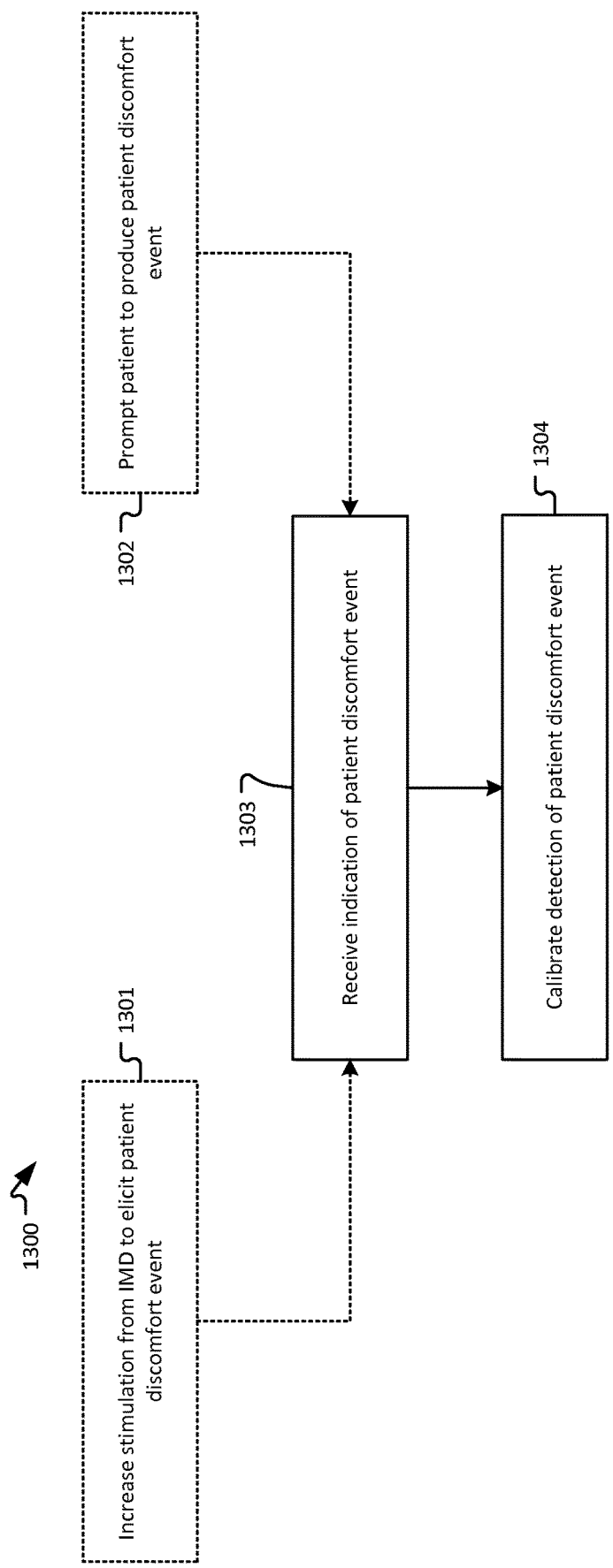

STIMULATION SUSPENSION IN RESPONSE TO PATIENT DISCOMFORT OR STATE

CROSS-REFERENCE TO RELATED PATENT APPLICATIONS

This application claims priority to and the benefit of U.S. Provisional Patent Application No. 62/237,078, filed Oct. 5, 2015, which is hereby incorporated by reference in its entirety.

FIELD

This application relates to neurostimulation and, more specifically, to improved systems and methods for detecting and managing stimulation therapy discomfort or side effects.

BACKGROUND

Chronic heart failure (CHF) and other forms of chronic cardiac dysfunction (CCD) may be related to an autonomic imbalance of the sympathetic and parasympathetic nervous systems that, if left untreated, can lead to cardiac arrhythmogenesis, progressively worsening cardiac function and eventual patient death. CHF is pathologically characterized by an elevated neuroexitatory state and is accompanied by physiological indications of impaired arterial and cardiopulmonary baroreflex function with reduced vagal activity.

CHF triggers compensatory activations of the sympathoadrenal (sympathetic) nervous system and the renin-angiotensin-aldosterone hormonal system, which initially helps to compensate for deteriorating heart-pumping function, yet, over time, can promote progressive left ventricular dysfunction and deleterious cardiac remodeling. Patients suffering from CHF are at increased risk of tachyarrhythmias, such as atrial fibrillation (AF), ventricular tachyarrhythmias (ventricular tachycardia (VT) and ventricular fibrillation (VF)), and atrial flutter, particularly when the underlying morbidity is a form of coronary artery disease, cardiomyopathy, mitral valve prolapse, or other valvular heart disease. Sympathoadrenal activation also significantly increases the risk and severity of tachyarrhythmias due to neuronal action of the sympathetic nerve fibers in, on, or around the heart and through the release of epinephrine (adrenaline), which can exacerbate an already-elevated heart rate.

The standard of care for managing CCD in general continues to evolve. For instance, new therapeutic approaches that employ electrical stimulation of neural structures that directly address the underlying cardiac autonomic nervous system imbalance and dysregulation have been proposed. In one form, controlled stimulation of the cervical vagus nerve beneficially modulates cardiovascular regulatory function. Vagus nerve stimulation (VNS) has been used for the clinical treatment of drug-refractory epilepsy and depression, and more recently has been proposed as a therapeutic treatment of heart conditions such as CHF. For instance, VNS has been demonstrated in canine studies as efficacious in simulated treatment of AF and heart failure, such as described in Zhang et al., "Chronic Vagus Nerve Stimulation Improves Autonomic Control and Attenuates Systemic Inflammation and Heart Failure Progression in a Canine High-Rate Pacing Model," Circ Heart Fail 2009, 2, pp. 692-699 (Sep. 22, 2009), the disclosure of which is incorporated by reference. The results of a multi-center open-label phase II study in which chronic VNS was utilized for CHF patients with severe systolic dysfunction is described in De Ferrari et al., "Chronic Vagus Nerve Stimulation: A New and Promising Therapeutic Approach for Chronic Heart Failure," European Heart Journal, 32, pp. 847-855 (Oct. 28, 2010).

VNS therapy commonly requires implantation of a neurostimulator, a surgical procedure requiring several weeks of recovery before the neurostimulator can be activated and a patient can start receiving VNS therapy. Even after the recovery and activation of the neurostimulator, a full therapeutic dose of VNS is not immediately delivered to the patient to avoid causing significant patient discomfort and other undesirable side effects. Instead, to allow the patient to adjust to the VNS therapy, a titration process is utilized in which the intensity is gradually increased over a period of time under a control of a physician, with the patient given time between successive increases in VNS therapy intensity to adapt to the new intensity. As stimulation is chronically applied at each new intensity level, the patient's tolerance threshold, or tolerance zone boundary, gradually increases, allowing for an increase in intensity during subsequent titration sessions. The titration process can take significantly longer in practice because the increase in intensity is generally performed by a physician or other healthcare provider, and thus, for every step in the titration process to take place, the patient has to visit the provider's office to have the titration performed. Scheduling conflicts in the provider's office may increase the time between titration sessions, thereby extending the overall titration process, during which the patient in need of VNS does not receive the VNS at the full therapeutic intensity.

For patients receiving VNS therapy for the treatment of epilepsy, a titration process that continues over an extended period of time, such as six to twelve months, may be somewhat acceptable because the patient's health condition typically would not worsen in that period of time. However, for patients being treated for other health conditions, such as CHF, the patient's condition may degrade rapidly if left untreated. As a result, there is a much greater urgency to completing the VNS titration process when treating a patient with a time-sensitive condition, such as CHF.

At the same time, some of the most common side effects which patients may experience during titration are coughing, throat irritation, and voice alteration. The VNS therapy may affect the patient's throat, for example, and may cause changes to the patient's voice or may cause irritation that results in coughing and throat irritation.

Accordingly, a need remains for an approach to efficiently titrate neurostimulation therapy for treating chronic cardiac dysfunction and other conditions while minimizing side effects and related discomfort caused by the titration or by the VNS therapy itself.

SUMMARY

Systems and methods are provided for delivering neurostimulation therapies to patients. In an embodiment, a method of suspending stimulation from an implantable medical device (IMD) in response to detecting a patient discomfort event may include detecting the patient discomfort event. The method may further include in response to detecting the patient discomfort event, suspending the stimulation from the IMD.

In various implementations one or more of the following features may be included. Detecting the patient discomfort event may include detecting the patient discomfort event during an ON cycle of the 1 MB. Suspending the stimulation from the IMD may include transitioning the IMD to an OFF cycle. Detecting the patient discomfort event may include detecting the patient discomfort event during an OFF cycle of the 1 MB. Suspending the stimulation from the IMD may include delaying initiation of an ON cycle of the 1 MB. The patient discomfort event may be a cough. The patient discomfort event may be associated with detecting a voice or a voice alteration of a patient. Detecting the patient discomfort event may include detecting the patient discomfort event via one or more of: an accelerometer, an acoustic sensor, an impedance sensor, a piezoelectric sensor, and a transthoracic impedance sensor. Suspending the stimulation from the 1 MB may include transitioning the 1 MB to an OFF cycle for the duration of a suspension period and transitioning the 1 MB to an ON cycle after the suspension period. Setting the suspension period may be based on a proximity of one or more parameters of the stimulation to one or more corresponding target stimulation parameters during a titration process. The suspension period may be based on a patient physical state. The patient physical state may be selected from the group consisting of sleeping, lying down, awake, sitting, standing, and moving.

In various implementations, the method may include assessing a severity level of the patient discomfort event. The method may further include setting the suspension period based on the severity level of the patient discomfort event. The method may also include determining a patient discomfort event response level based on a response of a patient to the suspension period. The method may additionally include adjusting the suspension period based on comparing the patient discomfort event response level to a patient discomfort event response threshold. Determining the patient discomfort event response level may include detecting one or more additional patient discomfort events. Adjusting the suspension period may include nonlinearly increasing or decreasing the suspension period.

In an embodiment, a method for calibrating detection of a patient discomfort event may include receiving an indication of the patient discomfort event. The method may further include calibrating detection of the patient discomfort event based on a patient discomfort event value received from a sensor. The patient discomfort event value may correspond to the patient discomfort event.

In various implementations, one or more of the following features may be included. The method may include increasing stimulation from an implantable medical device (IMD) to elicit the patient discomfort event. The method may further include prompting a patient to produce the patient discomfort event. Calibrating detection of the patient discomfort event may include calibrating detection of the patient discomfort event automatically via a programmer. Calibrating detection of the patient discomfort event may include calibrating detection of the patient discomfort event manually via a programmer. The sensor may be selected from the group consisting of an accelerometer, an acoustic sensor, an impedance sensor, a piezoelectric sensor, and a transthoracic impedance sensor. The indication of the patient discomfort event may be received from the sensor. The indication of the patient discomfort event may be received from a patient. The patient discomfort event may be a cough. The patient discomfort event may be associated with a voice or a voice alteration of a patient. The method may additionally include determining a qualification window corresponding to a window of time for which a true patient discomfort event may be detected. Moreover, the method may include logging results of an evaluation during a training session while determining a qualification window. The method may also include performing a root cause analysis based on the logged results to determine whether the patient discomfort event is attributable to stimulation from an IMD or attributable to another cause.

In an embodiment, a method for suspending stimulation from an implantable medical device (IMD) in response to detecting a patient discomfort event may include detecting the patient discomfort event via a sensor in the 1 MB. The method may further include assessing a severity level of the patient discomfort event based on a patient discomfort event value received from the sensor. The method may also include, in response to detecting the patient discomfort event, suspending the stimulation from the 1 MB by at least one of transitioning the IMD to an OFF cycle for the duration of a suspension period and transitioning the 1 MB to an ON cycle after the suspension period. The suspension period may be based on the severity level of the patient discomfort event and a patient physical state.

In an embodiment, an implantable medical device (IMD) includes a sensor, a processor coupled to the sensor and a memory operably coupled to the processor and comprising instructions that, when executed by the processor, cause the processor to detect a patient discomfort event via the sensor, determine a suspension period based on a severity of the patient discomfort event, the severity of the patient discomfort event determined using data received by the processor from the sensor, and in response to detecting the patient discomfort event, suspend the stimulation from the IMD for a duration of the suspension period. The processor may detect the patient discomfort event during an ON cycle of the IMD and suspend the stimulation from the IMD by transitioning the IMD to an OFF cycle. The processor may detect the patient discomfort event during an OFF cycle of the IMD and suspend the stimulation from the 1 MB by delaying initiation of an ON cycle of the 1 MB. Suspending the stimulation from the IMD may include transitioning the 1 MB to an OFF cycle for the duration of the suspension period and transitioning the IMD to an ON cycle after the suspension period. The processor may set the suspension period based on a proximity of one or more parameters of the stimulation to one or more corresponding target stimulation parameters during a titration process. The suspension period may be based on a patient physical state. The processor may determine a patient discomfort event response level based on a response of a patient to the suspension period and adjust the suspension period based on a comparison of the patient discomfort event response level to a patient discomfort event response threshold. Determining the patient discomfort event response level may include detecting one or more additional patient discomfort events. Adjusting the suspension period may include nonlinearly increasing or decreasing the suspension period.

In various implementations, one or more of the following features may be included. The sensor may be selected from the group consisting of an accelerometer, an acoustic sensor, an impedance sensor, a piezoelectric sensor, and a transthoracic impedance sensor. The patient physical state may be at least one of sleeping, lying down, awake, sitting, standing, and moving. The patient discomfort event may be a cough. The patient discomfort event may be associated with detecting a voice or a voice alteration of a patient. The suspension period may be longer based on the patient physical state being at least one of sleeping and lying down as compared to the physical state being at least one of awake, sitting, and standing.

Still other embodiments of the present invention will become readily apparent to those skilled in the art from the following detailed description, wherein are described embodiments by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

BRIEF DESCRIPTION OF DRAWINGS

FIG. 5 is a graph showing, by way of example, the relationship between the targeted therapeutic efficacy and the extent of potential side effects resulting from use of the implantable neurostimulator of FIG. 1.

FIG. 6 is a graph showing, by way of example, the optimal duty cycle range based on the intersection depicted in FIG. 5.

FIG. 7 is a timing diagram showing, by way of example, a stimulation cycle and an inhibition cycle of VNS as provided by implantable neurostimulator of FIG. 1.

FIGS. 8A-8C are illustrative charts reflecting a heart rate response to gradually increased stimulation intensity at different frequencies.

FIGS. 11A-11B are block diagrams of neurostimulation systems in accordance with embodiments of the present invention.

FIG. 13 is a calibration process in accordance with embodiments of the present invention.

DETAILED DESCRIPTION

CHF and other cardiovascular diseases cause derangement of autonomic control of the cardiovascular system, favoring increased sympathetic and decreased parasympathetic central outflow. These changes are accompanied by elevation of basal heart rate arising from chronic sympathetic hyperactivation along the neurocardiac axis.

The vagus nerve is a diverse nerve trunk that contains both sympathetic and parasympathetic fibers, and both afferent and efferent fibers. These fibers have different diameters and myelination, and subsequently have different activation thresholds. This results in a graded response as intensity is increased. Low intensity stimulation results in a progressively greater tachycardia, which then diminishes and is replaced with a progressively greater bradycardia response as intensity is further increased. Peripheral neurostimulation therapies that target the fluctuations of the autonomic nervous system have been shown to improve clinical outcomes in some patients. Specifically, autonomic regulation therapy results in simultaneous creation and propagation of efferent and afferent action potentials within nerve fibers comprising the cervical vagus nerve. The therapy directly improves autonomic balance by engaging both medullary and cardiovascular reflex control components of the autonomic nervous system. Upon stimulation of the cervical vagus nerve, action potentials propagate away from the stimulation site in two directions, efferently toward the heart and afferently toward the brain. Efferent action potentials influence the intrinsic cardiac nervous system and the heart and other organ systems, while afferent action potentials influence central elements of the nervous system.

Figure 1:
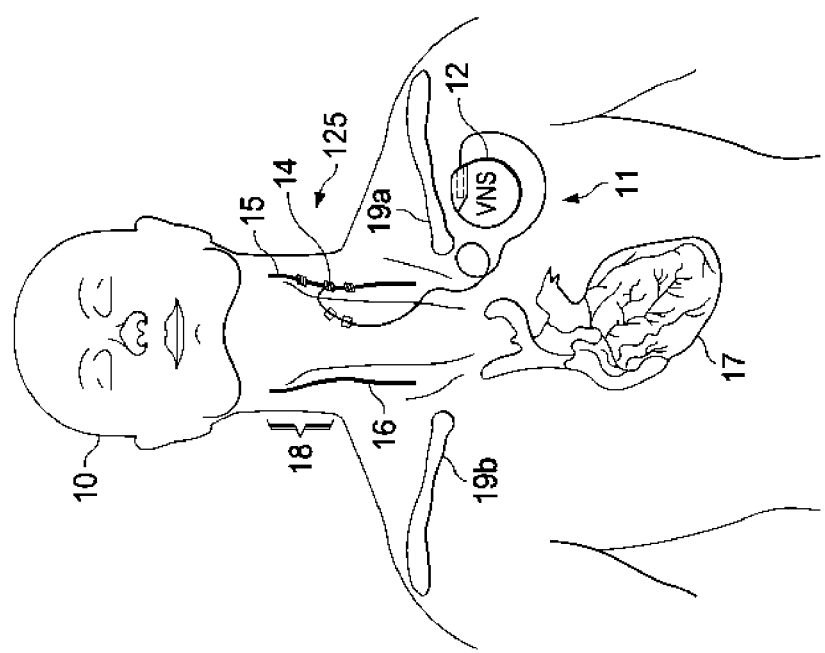
FIG. 1 is a front anatomical diagram showing, by way of example, placement of an implantable vagus stimulation device in a male patient, in accordance with one embodiment.

An implantable vagus nerve stimulator, such as used to treat drug-refractory epilepsy and depression, can be adapted for use in managing chronic cardiac dysfunction (CCD) through therapeutic bi-directional vagus nerve stimulation. FIG. 1 is a front anatomical diagram showing, by way of example, placement of an implantable medical device (e.g., a vagus nerve stimulation (VNS) system 11, as shown in FIG. 1) in a male patient 10, in accordance with embodiments of the present invention. The VNS provided through the stimulation system 11 operates under several mechanisms of action. These mechanisms include increasing parasympathetic outflow and inhibiting sympathetic effects by inhibiting norepinephrine release and adrenergic receptor activation. More importantly, VNS triggers the release of the endogenous neurotransmitter acetylcholine and other peptidergic substances into the synaptic cleft, which has several beneficial anti-arrhythmic, anti-apoptotic, and anti-inflammatory effects as well as beneficial effects at the level of the central nervous system.

The implantable vagus stimulation system 11 comprises an implantable neurostimulator or pulse generator 12 and a stimulating nerve electrode assembly 125. The stimulating nerve electrode assembly 125, preferably comprising at least an electrode pair, is conductively connected to the distal end of an insulated, electrically conductive lead assembly 13 and electrodes 14. The electrodes 14 may be provided in a variety of forms, such as, e.g., helical electrodes, probe electrodes, cuff electrodes, as well as other types of electrodes.

Figure 3:
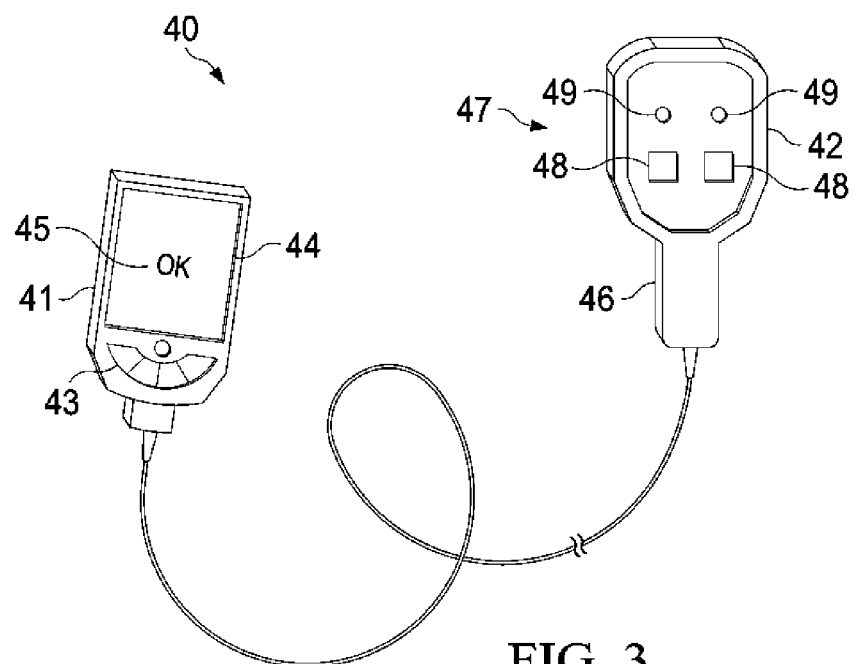
FIG. 3 is a diagram showing an external programmer for use with the implantable neurostimulator of FIG. 1.

The implantable vagus stimulation system 11 can be remotely accessed following implant through an external programmer, such as the programmer 40 shown in FIG. 3 and described in further detail below. The programmer 40 can be used by healthcare professionals to check and program the neurostimulator 12 after implantation in the patient 10 and to adjust stimulation parameters during the initial stimulation titration process. In some embodiments, an external magnet may provide basic controls, such as described in commonly assigned U.S. Pat. No. 8,600,505, entitled "Implantable Device For Facilitating Control Of Electrical Stimulation Of Cervical Vagus Nerves For Treatment Of Chronic Cardiac Dysfunction," the disclosure of which is incorporated by reference. For further example, an electromagnetic controller may enable the patient 10 or healthcare professional to interact with the implanted neurostimulator 12 to exercise increased control over therapy delivery and suspension, such as described in commonly-assigned U.S. Pat. No. 8,571,654, entitled "Vagus Nerve Neurostimulator With Multiple Patient-Selectable Modes For Treating Chronic Cardiac Dysfunction," the disclosure of which is incorporated by reference. For further example, an external programmer may communicate with the neurostimulation system 11 via other wired or wireless communication methods, such as, e.g., wireless RF transmission.

Together, the implantable vagus stimulation system 11 and one or more of the external components form a VNS therapeutic delivery system.

The neurostimulator 12 is typically implanted in the patient's right or left pectoral region generally on the same side (ipsilateral) as the vagus nerve 15, 16 to be stimulated, although other neurostimulator-vagus nerve configurations, including contra-lateral and bi-lateral are possible. A vagus nerve typically comprises two branches that extend from the brain stem respectively down the left side and right side of the patient, as seen in FIG. 1. The electrodes 14 are generally implanted on the vagus nerve 15, 16 about halfway between the clavicle 19*a*-*b* and the mastoid process. The electrodes may be implanted on either the left or right side. The lead assembly 13 and electrodes 14 are implanted by first exposing the carotid sheath and chosen branch of the vagus nerve 15, 16 through a latero-cervical incision (perpendicular to the long axis of the spine) on the ipsilateral side of the patient's neck 18. The helical electrodes 14 are then placed onto the exposed nerve sheath and tethered. A subcutaneous tunnel is formed between the respective implantation sites of the neurostimulator 12 and helical electrodes 14, through which the lead assembly 13 is guided to the neurostimulator 12 and securely connected.

In one embodiment, the neural stimulation is provided as a low level maintenance dose independent of cardiac cycle. The stimulation system 11 bi-directionally stimulates either the left vagus nerve 15 or the right vagus nerve 16. However, it is contemplated that multiple electrodes 14 and multiple leads 13 could be utilized to stimulate simultaneously, alternatively or in other various combinations. Stimulation may be through multimodal application of continuously-cycling, intermittent and periodic electrical stimuli, which are parametrically defined through stored stimulation parameters and timing cycles. Both sympathetic and parasympathetic nerve fibers in the vagosympathetic complex are stimulated. A study of the relationship between cardiac autonomic nerve activity and blood pressure changes in ambulatory dogs is described in J. Hellyer et al., "Autonomic Nerve Activity and Blood Pressure in Ambulatory Dogs," Heart Rhythm, Vol. 11(2), pp. 307-313 (February 2014). Generally, cervical vagus nerve stimulation results in propagation of action potentials from the site of stimulation in a bi-directional manner. The application of bi-directional propagation in both afferent and efferent directions of action potentials within neuronal fibers comprising the cervical vagus nerve improves cardiac autonomic balance. Afferent action potentials propagate toward the parasympathetic nervous system's origin in the medulla in the nucleus ambiguus, nucleus tractus solitarius, and the dorsal motor nucleus, as well as towards the sympathetic nervous system's origin in the intermediolateral cell column of the spinal cord. Efferent action potentials propagate toward the heart 17 to activate the components of the heart's intrinsic nervous system. Either the left or right vagus nerve 15, 16 can be stimulated by the stimulation system 11. The right vagus nerve 16 has a moderately lower (approximately 30%) stimulation threshold than the left vagus nerve 15 for heart rate effects at the same stimulation frequency and pulse width.

Figure 2B:
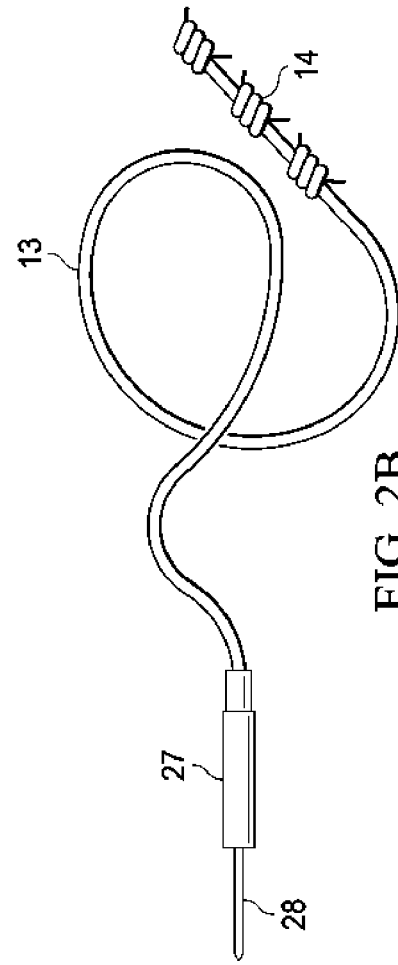
FIGS. 2A and 2B are diagrams respectively showing the implantable neurostimulator and the simulation therapy lead of FIG. 1.
Figure 2A:
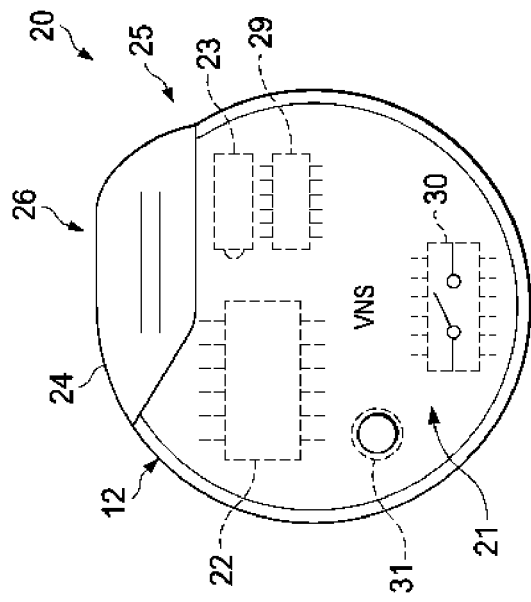

The VNS therapy is delivered autonomously to the patient's vagus nerve 15, 16 through three implanted components that include a neurostimulator 12, lead assembly 13, and electrodes 14. FIGS. 2A and 2B are diagrams respectively showing the implantable neurostimulator 12 and the stimulation lead assembly 13 of FIG. 1. In one embodiment, the neurostimulator 12 can be adapted from a VNS Therapy Demipulse Model 103 or AspireSR Model 106 pulse generator, manufactured and sold by Cyberonics, Inc., Houston, Tex., although other manufactures and types of implantable VNS neurostimulators could also be used. The stimulation lead assembly 13 and electrodes 14 are generally fabricated as a combined assembly and can be adapted from a Model 302 lead, PerenniaDURA Model 303 lead, or PerenniaFLEX Model 304 lead, also manufactured and sold by Cyberonics, Inc., in three sizes based, for example, on a helical electrode inner diameter, although other manufactures and types of single-pin receptacle-compatible therapy leads and electrodes could also be used.

Referring first to FIG. 2A, the system 20 may be configured to provide multimodal vagus nerve stimulation. In a maintenance mode, the neurostimulator 12 is parametrically programmed to deliver continuously-cycling, intermittent and periodic ON-OFF cycles of VNS. Such delivery produces action potentials in the underlying nerves that propagate bi-directionally, both afferently and efferently.

The neurostimulator 12 includes an electrical pulse generator that is tuned to improve autonomic regulatory function by triggering action potentials that propagate both afferently and efferently within the vagus nerve 15, 16. The neurostimulator 12 is enclosed in a hermetically sealed housing 21 constructed of a biocompatible material, such as titanium. The housing 21 contains electronic circuitry 22 powered by a battery 23, such as a lithium carbon monofluoride primary battery or a rechargeable secondary cell battery. The electronic circuitry 22 may be implemented using complementary metal oxide semiconductor integrated circuits that include a microprocessor controller that executes a control program according to stored stimulation parameters and timing cycles; a voltage regulator that regulates system power; logic and control circuitry, including a recordable memory 29 within which the stimulation parameters are stored, that controls overall pulse generator function, receives and implements programming commands from the external programmer, or other external source, collects and stores telemetry information, processes sensory input, and controls scheduled and sensory-based therapy outputs; a transceiver that remotely communicates with the external programmer using radio frequency signals; an antenna, which receives programming instructions and transmits the telemetry information to the external programmer; and a reed switch 30 that provides remote access to the operation of the neurostimulator 12 using an external programmer, a simple patient magnet, or an electromagnetic controller. The recordable memory 29 can include both volatile (dynamic) and non-volatile/persistent (static) forms of memory, within which the stimulation parameters and timing cycles can be stored. Other electronic circuitry and components are possible.

The neurostimulator 12 includes a header 24 to securely receive and connect to the lead assembly 13. In one embodiment, the header 24 encloses a receptacle 25 into which a single pin for the lead assembly 13 can be received, although two or more receptacles could also be provided, along with the corresponding electronic circuitry 22. The header 24 internally includes a lead connector block (not shown), a setscrew, and a spring contact (not shown) that electrically connects to the lead ring, thus completing the electrical circuit 26.

In some embodiments, the housing 21 may also contain a heart rate sensor 31 that is electrically interfaced with the logic and control circuitry, which receives the patient's sensed heart rate as sensory inputs. The heart rate sensor 31 monitors heart rate using an ECG-type electrode. Through the electrode, the patient's heart beat can be sensed by detecting ventricular depolarization. In a further embodiment, a plurality of electrodes can be used to sense voltage differentials between electrode pairs, which can undergo signal processing for cardiac physiological measures, for instance, detection of the P-wave, QRS complex, and T-wave. The heart rate sensor 31 provides the sensed heart rate to the control and logic circuitry as sensory inputs that can be used to determine the onset or presence of arrhythmias, particularly VT, and/or to monitor and record changes in the patient's heart rate over time or in response to applied stimulation signals.

Referring next to FIG. 2B, the lead assembly 13 delivers an electrical signal from the neurostimulator 12 to the vagus nerve 15, 16 via the electrodes 14. On a proximal end, the lead assembly 13 has a lead connector 27 that transitions an insulated electrical lead body to a metal connector pin 28 and metal connector ring. During implantation, the connector pin 28 is guided through the receptacle 25 into the header 24 and securely fastened in place using the setscrew 26 to electrically couple one electrode of the lead assembly 13 to the neurostimulator 12 while the spring contact makes electrical contact to the ring connected to the other electrode. On a distal end, the lead assembly 13 terminates with the electrode 14, which bifurcates into a pair of anodic and cathodic electrodes 62 (as further described infra with reference to FIG. 4). In one embodiment, the lead connector 27 is manufactured using silicone and the connector pin 28 and ring are made of stainless steel, although other suitable materials could be used, as well. The insulated lead body 13 utilizes a silicone-insulated alloy conductor material.

In some embodiments, the electrodes 14 are helical and placed around the cervical vagus nerve 15, 16 at the location below where the superior and inferior cardiac branches separate from the cervical vagus nerve. In alternative embodiments, the helical electrodes may be placed at a location above where one or both of the superior and inferior cardiac branches separate from the cervical vagus nerve. In one embodiment, the helical electrodes 14 are positioned around the patient's vagus nerve oriented with the end of the helical electrodes 14 facing the patient's head. In an alternate embodiment, the helical electrodes 14 are positioned around the patient's vagus nerve 15, 16 oriented with the end of the helical electrodes 14 facing the patient's heart 17. At the distal end, the insulated electrical lead body 13 is bifurcated into a pair of lead bodies that are connected to a pair of electrodes. The polarity of the electrodes could be configured into a proximal anode and a distal cathode, or a proximal cathode and a distal anode.

The neurostimulator 12 may be interrogated prior to implantation and throughout the therapeutic period with a healthcare provider-operable control system comprising an external programmer and programming wand (shown in FIG. 3) for checking proper operation, downloading recorded data, diagnosing problems, and programming operational parameters, such as described in commonly-assigned U.S. Pat. Nos. 8,600,505 and 8,571,654, cited supra. FIG. 3 is a diagram showing an external programmer 40 for use with the implantable neurostimulator 12 of FIG. 1. The external programmer 40 includes a healthcare provider operable programming computer 41 and a programming wand 42. Generally, use of the external programmer is restricted to healthcare providers, while more limited manual control is provided to the patient through "magnet mode."

In one embodiment, the external programmer 40 executes application software 45 specifically designed to interrogate the neurostimulator 12. The programming computer 41 interfaces to the programming wand 42 through a wired or wireless data connection. The programming wand 42 can be adapted from a Model 201 Programming Wand, manufactured and sold by Cyberonics, Inc., and the application software 45 can be adapted from the Model 250 Programming Software suite, licensed by Cyberonics, Inc. Other configurations and combinations of external programmer 40, programming wand 42 and application software 45 are possible.

The programming computer 41 can be implemented using a general purpose programmable computer and can be a personal computer, laptop computer, ultrabook computer, netbook computer, handheld computer, tablet computer, smart phone, or other form of computational device. In one embodiment, the programming computer is a tablet computer that may operate under the iOS operating system from Apple Inc., such as the iPad from Apple Inc., or may operate under the Android operating system from Google Inc., such as the Galaxy Tab from Samsung Electronics Co., Ltd. In an alternative embodiment, the programming computer is a personal digital assistant handheld computer operating under the Pocket-PC, Windows Mobile, Windows Phone, Windows RT, or Windows operating systems, licensed by Microsoft Corporation, Redmond, Wash., such as the Surface from Microsoft Corporation, the Dell Axim X5 and X50 personal data assistants, sold by Dell, Inc., Round Top, Tex., the HP Jornada personal data assistant, sold by Hewlett-Packard Company, Palo Alto, Tex. The programming computer 41 functions through those components conventionally found in such devices, including, for instance, a central processing unit, volatile and persistent memory, touch-sensitive display, control buttons, peripheral input and output ports, and network interface. The computer 41 operates under the control of the application software 45, which is executed as program code as a series of process or method modules or steps by the programmed computer hardware. Other assemblages or configurations of computer hardware, firmware, and software are possible.

Operationally, the programming computer 41, when connected to a neurostimulator 12 through wireless telemetry using the programming wand 42, can be used by a healthcare provider to remotely interrogate the neurostimulator 12 and modify stored stimulation parameters. The programming wand 42 provides data conversion between the digital data accepted by and output from the programming computer and the radio frequency signal format that is required for communication with the neurostimulator 12. In other embodiments, the programming computer may communicate with the implanted neurostimulator 12 using other wireless communication methods, such as wireless RF transmission. The programming computer 41 may further be configured to receive inputs, such as physiological signals received from patient sensors (e.g., implanted or external). These sensors may be configured to monitor one or more physiological signals, e.g., vital signs, such as body temperature, pulse rate, respiration rate, blood pressure, etc. These sensors may be coupled directly to the programming computer 41 or may be coupled to another instrument or computing device which receives the sensor input and transmits the input to the programming computer 41. The programming computer 41 may monitor, record, and/or respond to the physiological signals in order to effectuate stimulation delivery in accordance with embodiments of the present invention.

The healthcare provider operates the programming computer 41 through a user interface that includes a set of input controls 43 and a visual display 44, which could be touch-sensitive, upon which to monitor progress, view downloaded telemetry and recorded physiology, and review and modify programmable stimulation parameters. The telemetry can include reports on device history that provide patient identifier, implant date, model number, serial number, magnet activations, total ON time, total operating time, manufacturing date, and device settings and stimulation statistics and on device diagnostics that include patient identifier, model identifier, serial number, firmware build number, implant date, communication status, output current status, measured current delivered, lead impedance, and battery status. Other kinds of telemetry or telemetry reports are possible.

During interrogation, the programming wand 42 is held by its handle 46 and the bottom surface 47 of the programming wand 42 is placed on the patient's chest over the location of the implanted neurostimulator 12. A set of indicator lights 49 can assist with proper positioning of the wand and a set of input controls 48 enable the programming wand 42 to be operated directly, rather than requiring the healthcare provider to awkwardly coordinate physical wand manipulation with control inputs via the programming computer 41. The sending of programming instructions and receipt of telemetry information occur wirelessly through radio frequency signal interfacing. Other programming computer and programming wand operations are possible.

Figure 4:
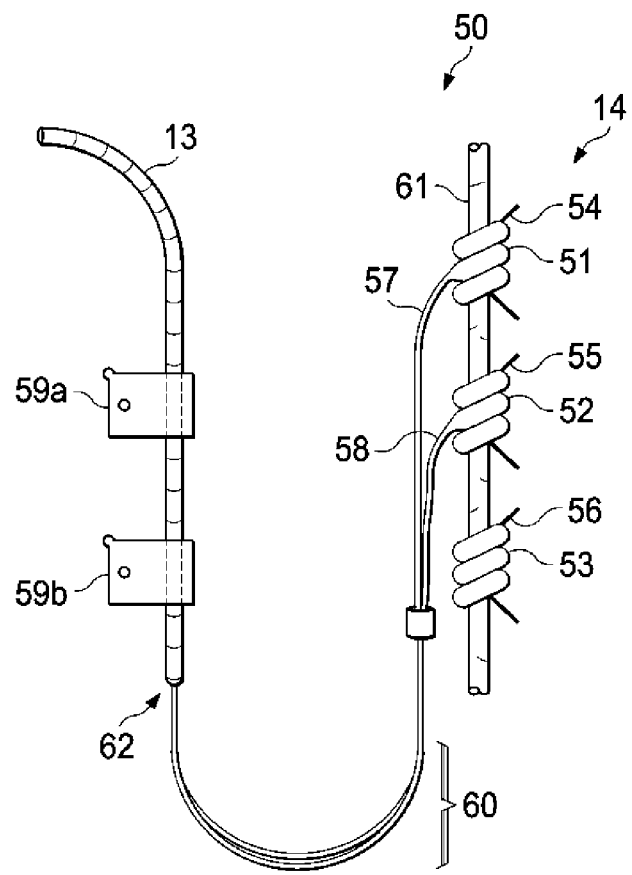
FIG. 4 is a diagram showing electrodes provided as on the stimulation therapy lead of FIG. 2 in place on a vagus nerve in situ.

FIG. 4 is a diagram showing the helical electrodes 14 provided as on the stimulation lead assembly 13 of FIG. 2 in place on a vagus nerve 15, 16 in situ 50. Although described with reference to a specific manner and orientation of implantation, the specific surgical approach and implantation site selection particulars may vary, depending upon physician discretion and patient physical structure.

Under one embodiment, helical electrodes 14 may be positioned on the patient's vagus nerve 61 oriented with the end of the helical electrodes 14 facing the patient's head. At the distal end, the insulated electrical lead body 13 is bifurcated into a pair of lead bodies 57, 58 that are connected to a pair of electrodes 51, 52. The polarity of the electrodes 51, 52 could be configured into a proximal anode and a distal cathode, or a proximal cathode and a distal anode. In addition, an anchor tether 53 is fastened over the lead bodies 57, 58 that maintains the helical electrodes' position on the vagus nerve 61 following implant. In one embodiment, the conductors of the electrodes 51, 52 are manufactured using a platinum and iridium alloy, while the helical materials of the electrodes 51, 52 and the anchor tether 53 are a silicone elastomer.

During surgery, the electrodes 51, 52 and the anchor tether 53 are coiled around the vagus nerve 61 proximal to the patient's head, each with the assistance of a pair of sutures 54, 55, 56, made of polyester or other suitable material, which help the surgeon to spread apart the respective helices. The lead bodies 57, 58 of the electrodes 51, 52 are oriented distal to the patient's head and aligned parallel to each other and to the vagus nerve 61. A strain relief bend 60 can be formed on the distal end with the insulated electrical lead body 13 aligned, for example, parallel to the helical electrodes 14 and attached to the adjacent fascia by a plurality of tie-downs 59a-b.

The neurostimulator 12 delivers VNS under control of the electronic circuitry 22. The stored stimulation parameters are programmable. Each stimulation parameter can be independently programmed to define the characteristics of the cycles of therapeutic stimulation and inhibition to ensure optimal stimulation for a patient 10. The programmable stimulation parameters include output current, signal frequency, pulse width, signal ON time, signal OFF time, magnet activation (for VNS specifically triggered by "magnet mode"), and reset parameters. Other programmable parameters are possible. In addition, sets or "profiles" of preselected stimulation parameters can be provided to physicians with the external programmer and fine-tuned to a patient's physiological requirements prior to being programmed into the neurostimulator 12, such as described in commonly-assigned U.S. Pat. No. 8,630,709, entitled "Computer-Implemented System and Method for Selecting Therapy Profiles of Electrical Stimulation of Cervical Vagus Nerves for Treatment of Chronic Cardiac Dysfunction," the disclosure of which is incorporated by reference.

Therapeutically, the VNS may be delivered as a multimodal set of therapeutic doses, which are system output behaviors that are pre-specified within the neurostimulator 12 through the stored stimulation parameters and timing cycles implemented in firmware and executed by the microprocessor controller. The therapeutic doses include a maintenance dose that includes continuously-cycling, intermittent and periodic cycles of electrical stimulation during periods in which the pulse amplitude is greater than 0 mA ("therapy ON") and during periods in which the pulse amplitude is 0 mA ("therapy OFF").

The neurostimulator 12 can operate either with or without an integrated heart rate sensor, such as respectively described in commonly-assigned U.S. Pat. No. 8,577,458, entitled "Implantable Device for Providing Electrical Stimulation of Cervical Vagus Nerves for Treatment of Chronic Cardiac Dysfunction with Leadless Heart Rate Monitoring," and U.S. patent application, entitled "Implantable Device for Providing Electrical Stimulation of Cervical Vagus Nerves for Treatment of Chronic Cardiac Dysfunction," Ser. No. 13/314,119, filed on Dec. 7, 2011, pending, the disclosures of which are hereby incorporated by reference herein in their entirety. Additionally, where an integrated leadless heart rate monitor is available, the neurostimulator 12 can provide autonomic cardiovascular drive evaluation and self-controlled titration, such as respectively described in commonly-assigned U.S. patent application entitled "Implantable Device for Evaluating Autonomic Cardiovascular Drive in a Patient Suffering from Chronic Cardiac Dysfunction," Ser. No. 13/314,133, filed on Dec. 7, 2011, U.S. Patent Publication No. 2013-0158616 A1, pending, and U.S. patent application entitled "Implantable Device for Providing Electrical Stimulation of Cervical Vagus Nerves for Treatment of Chronic Cardiac Dysfunction with Bounded Titration," Ser. No. 13/314,135, filed on Dec. 7, 2011, U.S. Patent Publication No. 2013-0158617 A1, pending, the disclosures of which are incorporated by reference. Finally, the neurostimulator 12 can be used to counter natural circadian sympathetic surge upon awakening and manage the risk of cardiac arrhythmias during or attendant to sleep, particularly sleep apneic episodes, such as respectively described in commonly-assigned U.S. patent application entitled "Implantable Neurostimulator-Implemented Method For Enhancing Heart Failure Patient Awakening Through Vagus Nerve Stimulation," Ser. No. 13/673,811, filed on Nov. 9, 2012, U.S. Patent Publication No. 2014-0135864-A1, pending, the disclosure of which is incorporated by reference.

The VNS stimulation signal may be delivered as a therapy in a maintenance dose having an intensity that is insufficient to elicit undesirable side effects, such as cardiac arrhythmias. The VNS can be delivered with a periodic duty cycle in the range of 2% to 89% with a preferred range of around 4% to 36% that is delivered as a low intensity maintenance dose. Alternatively, the low intensity maintenance dose may comprise a narrow range approximately at 17.5%, such as around 15% to 25%. The selection of duty cycle is a tradeoff among competing medical considerations. The duty cycle is determined by dividing the stimulation ON time by the sum of the ON and OFF times of the neurostimulator 12 during a single ON-OFF cycle. However, the stimulation time may also need to include ramp-up time and ramp-down time, where the stimulation frequency exceeds a minimum threshold (as further described infra with reference to FIG. 7).

FIG. 5 is a graph 70 showing, by way of example, the relationship between the targeted therapeutic efficacy 73 and the extent of potential side effects 74 resulting from use of the implantable neurostimulator 12 of FIG. 1, after the patient has completed the titration process. The graph in FIG. 5 provides an illustration of the failure of increased stimulation intensity to provide additional therapeutic benefit, once the stimulation parameters have reached the neural fulcrum zone, as will be described in greater detail below with respect to FIG. 8. As shown in FIG. 5, the x-axis represents the duty cycle 71. The duty cycle is determined by dividing the stimulation ON time by the sum of the ON and OFF times of the neurostimulator 12 during a single ON-OFF cycle. However, the stimulation time may also include ramp-up time and ramp-down time, where the stimulation frequency exceeds a minimum threshold (as further described infra with reference to FIG. 7). When including the ramp-up and ramp-down times, the total duty cycle may be calculated as the ON time plus the ramp-up and ramp-down times divided by the OFF time, ON time, and ramp-up and ramp-down times, and may be, e.g., between 15% and 30%, and more specifically approximately 23%. The y-axis represents physiological response 72 to VNS therapy. The physiological response 72 can be expressed quantitatively for a given duty cycle 71 as a function of the targeted therapeutic efficacy 73 and the extent of potential side effects 74, as described infra. The maximum level of physiological response 72 ("max") signifies the highest point of targeted therapeutic efficacy 73 or potential side effects 74.

Targeted therapeutic efficacy 73 and the extent of potential side effects 74 can be expressed as functions of duty cycle 71 and physiological response 72. The targeted therapeutic efficacy 73 represents the intended effectiveness of VNS in provoking a beneficial physiological response for a given duty cycle and can be quantified by assigning values to the various acute and chronic factors that contribute to the physiological response 72 of the patient 10 due to the delivery of therapeutic VNS. Acute factors that contribute to the targeted therapeutic efficacy 73 include beneficial changes in heart rate variability and increased coronary flow, reduction in cardiac workload through vasodilation, and improvement in left ventricular relaxation. Chronic factors that contribute to the targeted therapeutic efficacy 73 include improved cardiovascular regulatory function, as well as decreased negative cytokine production, increased baroreflex sensitivity, increased respiratory gas exchange efficiency, favorable gene expression, renin-angiotensin-aldosterone system down-regulation, anti-arrhythmic, anti-apoptotic, and ectopy-reducing anti-inflammatory effects. These contributing factors can be combined in any manner to express the relative level of targeted therapeutic efficacy 73, including weighting particular effects more heavily than others or applying statistical or numeric functions based directly on or derived from observed physiological changes. Empirically, targeted therapeutic efficacy 73 steeply increases beginning at around a 5% duty cycle, and levels off in a plateau near the maximum level of physiological response at around a 30% duty cycle. Thereafter, targeted therapeutic efficacy 73 begins decreasing at around a 50% duty cycle and continues in a plateau near a 25% physiological response through the maximum 100% duty cycle.

The intersection 75 of the targeted therapeutic efficacy 73 and the extent of potential side effects 74 represents one optimal duty cycle range for VNS. FIG. 6 is a graph 80 showing, by way of example, the optimal duty cycle range 83 based on the intersection 75 depicted in FIG. 5. The x-axis represents the duty cycle 81 as a percentage of stimulation time over stimulation time plus inhibition time. The y-axis represents therapeutic points 82 reached in operating the neurostimulator 12 at a given duty cycle 81. The optimal duty cycle range 83 is a function 84 of the intersection 75 of the targeted therapeutic efficacy 73 and the extent of potential side effects 74. The therapeutic operating points 82 can be expressed quantitatively for a given duty cycle 81 as a function of the values of the targeted therapeutic efficacy 73 and the extent of potential side effects 74 at the given duty cycle shown in the graph 70 of FIG. 5. The optimal therapeutic operating point 85 ("max") signifies a tradeoff that occurs at the point of highest targeted therapeutic efficacy 73 in light of lowest potential side effects 74 and that point will typically be found within the range of a 5% to 30% duty cycle 81. Other expressions of duty cycles and related factors are possible.

Therapeutically and in the absence of patient physiology of possible medical concern, such as cardiac arrhythmias, VNS is delivered in a low level maintenance dose that uses alternating cycles of stimuli application (ON) and stimuli inhibition (OFF) that are tuned to activate both afferent and efferent pathways. Stimulation results in parasympathetic activation and sympathetic inhibition, both through centrally-mediated pathways and through efferent activation of preganglionic neurons and local circuit neurons. FIG. 7 is a timing diagram showing, by way of example, a stimulation cycle and an inhibition cycle of VNS 90, as provided by implantable neurostimulator 12 of FIG. 1. The stimulation parameters enable the electrical stimulation pulse output by the neurostimulator 12 to be varied by both amplitude (output current 96) and duration (pulse width 94). The number of output pulses delivered per second determines the signal frequency 93. In one embodiment, a pulse width in the range of 100 to 250 μsec delivers between 0.02 mA and 50 mA of output current at a signal frequency of about 10 Hz, although other therapeutic values could be used as appropriate. In general, the stimulation signal delivered to the patient may be defined by a stimulation parameter set comprising at least an amplitude, a frequency, a pulse width, and a duty cycle.

In one embodiment, the stimulation time is considered the time period during which the neurostimulator 12 is ON and delivering pulses of stimulation, and the OFF time is considered the time period occurring in-between stimulation times during which the neurostimulator 12 is OFF and inhibited from delivering stimulation.

In another embodiment, as shown in FIG. 7, the neurostimulator 12 implements a stimulation time 91 comprising an ON time 92, a ramp-up time 97 and a ramp-down time 98 that respectively precede and follow the ON time 92. Under this embodiment, the ON time 92 is considered to be a time during which the neurostimulator 12 is ON and delivering pulses of stimulation at the full output current 96. Under this embodiment, the OFF time 95 is considered to comprise the ramp-up time 97 and ramp-down time 98, which are used when the stimulation frequency is at least 10 Hz, although other minimum thresholds could be used, and both ramp-up and ramp-down times 97, 98 last two seconds, although other time periods could also be used. The ramp-up time 97 and ramp-down time 98 allow the strength of the output current 96 of each output pulse to be gradually increased and decreased, thereby avoiding deleterious reflex behavior due to sudden delivery or inhibition of stimulation at a programmed intensity.

Therapeutic vagus neural stimulation has been shown to provide cardioprotective effects. Although delivered in a maintenance dose having an intensity that is insufficient to elicit undesirable side effects, such as cardiac arrhythmias, ataxia, coughing, hoarseness, throat irritation, voice alteration, or dyspnea, therapeutic VNS can nevertheless potentially ameliorate pathological tachyarrhythmias in some patients. Although VNS has been shown to decrease defibrillation threshold, VNS has not been shown to terminate VF in the absence of defibrillation. VNS prolongs ventricular action potential duration, so may be effective in terminating VT. In addition, the effect of VNS on the AV node may be beneficial in patients with AF by slowing conduction to the ventricles and controlling ventricular rate.

Neural Fulcrum Zone

As described above, autonomic regulation therapy results in simultaneous creation of action potentials that simultaneously propagate away from the stimulation site in afferent and efferent directions within axons comprising the cervical vagus nerve complex. Upon stimulation of the cervical vagus nerve, action potentials propagate away from the stimulation site in two directions, efferently toward the heart and afferently toward the brain. Different parameter settings for the neurostimulator 12 may be adjusted to deliver varying stimulation intensities to the patient. The various stimulation parameter settings for current VNS devices include output current amplitude, signal frequency, pulse width, signal ON time, and signal OFF time.

When delivering neurostimulation therapies to patients, it is generally desirable to avoid stimulation intensities that result in either excessive tachycardia or excessive bradycardia. However, researchers have typically utilized the patient's heart rate changes as a functional response indicator or surrogate for effective recruitment of nerve fibers and engagement of the autonomic nervous system elements responsible for regulation of heart rate, which may be indicative of therapeutic levels of VNS. Some researchers have proposed that heart rate reduction caused by VNS stimulation is itself beneficial to the patient.

In accordance with some embodiments, a neural fulcrum zone is identified, and neurostimulation therapy is delivered within the neural fulcrum zone. This neural fulcrum zone corresponds to a combination of stimulation parameters at which autonomic engagement is achieved but for which a functional response determined by heart rate change is nullified due to the competing effects of afferently and efferently-transmitted action potentials. In this way, the tachycardia-inducing stimulation effects are offset by the bradycardia-inducing effects, thereby minimizing side effects such as significant heart rate changes while providing a therapeutic level of stimulation. One method of identifying the neural fulcrum zone is by delivering a plurality of stimulation signals at a fixed frequency but with one or more other parameter settings changed so as to gradually increase the intensity of the stimulation.

Figure 8A:
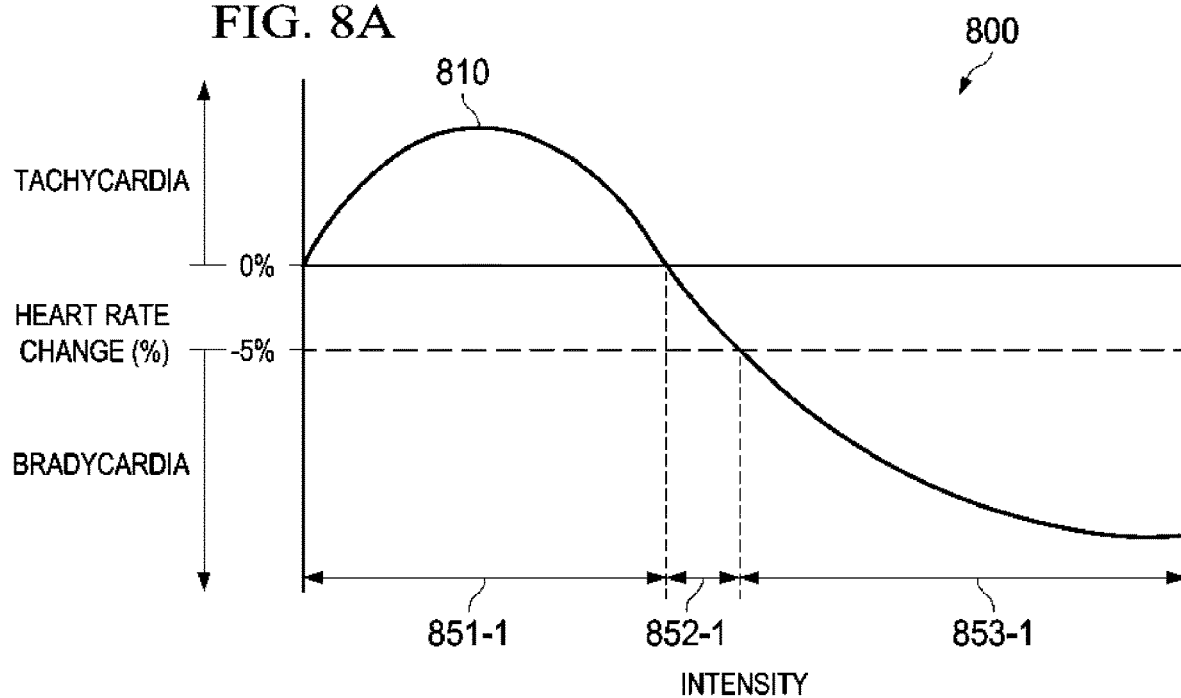
Figure 8B:
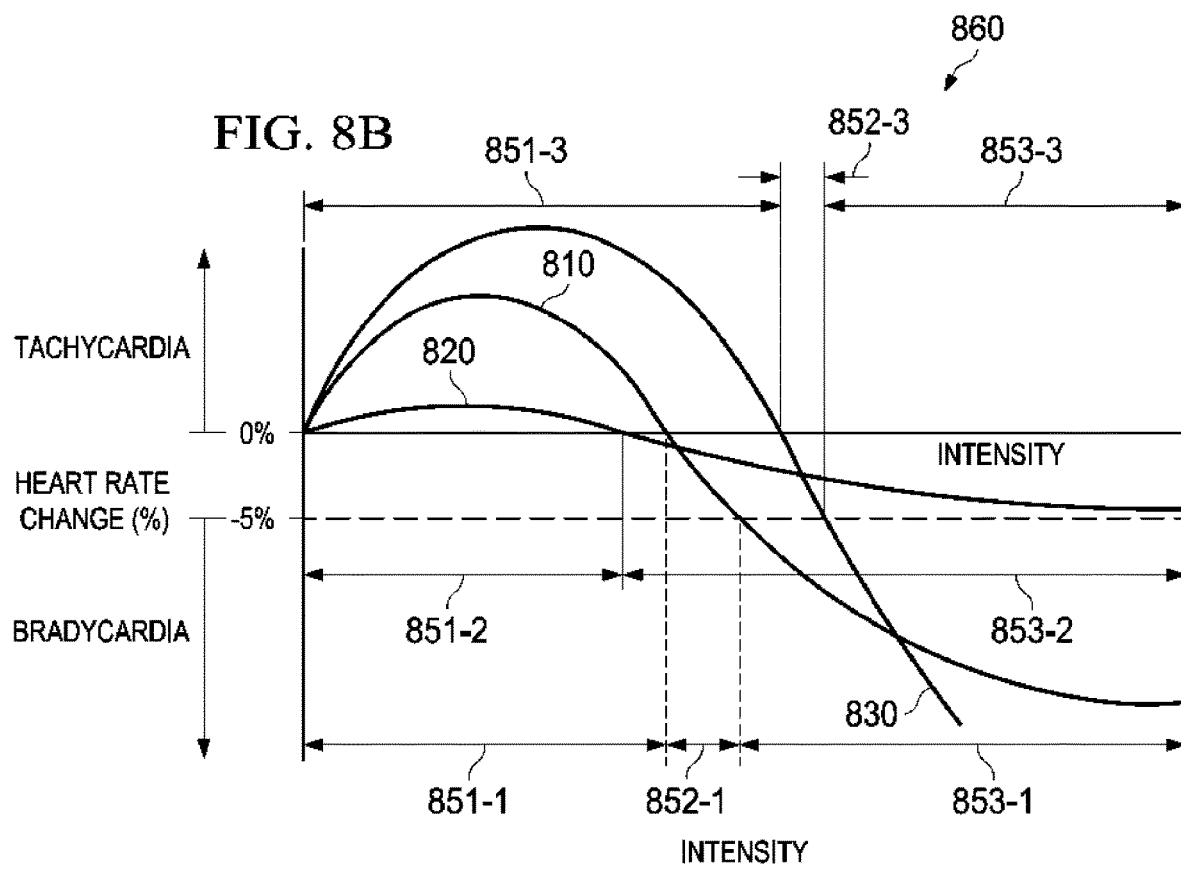

FIGS. 8A-8C provide illustrative charts reflecting the location of the neural fulcrum zone. FIG. 8A is a chart 800 illustrating a heart rate response in response to such a gradually increased intensity at a first frequency, in accordance with embodiments of the present invention. In this chart 800, the x-axis represents the intensity level of the stimulation signal, and the y-axis represents the observed heart rate change from the patient's baseline basal heart rate observed when no stimulation is delivered. In this example, the stimulation intensity is increased by increasing the output current amplitude.

A first set 810 of stimulation signals is delivered at a first frequency (e.g., 10 Hz). Initially, as the intensity (e.g., output current amplitude) is increased, a tachycardia zone 851-1 is observed, during which period, the patient experiences a mild tachycardia. As the intensity continues to be increased for subsequent stimulation signals, the patient's heart rate response begins to decrease and eventually enters a bradycardia zone 853-1, in which a bradycardia response is observed in response to the stimulation signals. As described above, the neural fulcrum zone is a range of stimulation parameters at which the functional effects from afferent activation are balanced with or nullified by the functional effects from efferent activation to avoid extreme heart rate changes while providing therapeutic levels of stimulation. In accordance with some embodiments, the neural fulcrum zone 852-1 can be located by identifying the zone in which the patient's response to stimulation produces either no heart rate change or a mildly decreased heart rate change (e.g., <5% decrease, or a target number of beats per minute). As the intensity of stimulation is further increased at the fixed first frequency, the patient enters an undesirable bradycardia zone 853-1. In these embodiments, the patient's heart rate response is used as an indicator of autonomic engagement. In other embodiments, other physiological responses may be used to indicate the zone of autonomic engagement at which the propagation of efferent and afferent action potentials are balanced, the neural fulcrum zone.

FIG. 8B is a chart 860 illustrating a heart rate response in response to such a gradually increased intensity at two additional frequencies, in accordance with embodiments of the present invention. In this chart 860, the x-axis and y-axis represent the intensity level of the stimulation signal and the observed heart rate change, respectively, as in FIG. 8A, and the first set 810 of stimulation signals from FIG. 8A is also shown.

A second set 810 of stimulation signals is delivered at a second frequency lower than the first frequency (e.g., 5 Hz). Initially, as the intensity (e.g., output current amplitude) is increased, a tachycardia zone 851-2 is observed, during which period, the patient experiences a mild tachycardia. As the intensity continues to be increased for subsequent stimulation signals, the patient's heart rate response begins to decrease and eventually enters a bradycardia zone 853-2, in which a bradycardia response is observed in response to the stimulation signals. The low frequency of the stimulation signal in the second set 820 of stimulation signals limits the functional effects of nerve fiber recruitment and, as a result, the heart response remains relatively limited. Although this low frequency stimulation results in minimal side effects, the stimulation intensity is too low to result in effective recruitment of nerve fibers and engagement of the autonomic nervous system. As a result, a therapeutic level of stimulation is not delivered.

A third set of 830 of stimulation signals is delivered at a third frequency higher than the first and second frequencies (e.g., 20 Hz). As with the first set 810 and second set 820, at lower intensities, the patient first experiences a tachycardia zone 851-3. At this higher frequency, the level of increased heart rate is undesirable. As the intensity is further increased, the heart rate decreases, similar to the decrease at the first and second frequencies but at a much higher rate. The patient first enters the neural fulcrum zone 852-3 and then the undesirable bradycardia zone 853-3. Because the slope of the curve for the third set 830 is much steeper than the second set 820, the region in which the patient's heart rate response is between 0% and −5% (e.g., the neural fulcrum zone 852-3) is much narrower than the neural fulcrum zone 852-2 for the second set 820. Accordingly, when testing different operational parameter settings for a patient by increasing the output current amplitude by incremental steps, it can be more difficult to locate a programmable output current amplitude that falls within the neural fulcrum zone 852-3. When the slope of the heart rate response curve is high, the resulting heart rate may overshoot the neural fulcrum zone and create a situation in which the functional response transitions from the tachycardia zone 851-3 to the undesirable bradycardia zone 853-3 in a single step. At that point, the clinician would need to reduce the amplitude by a smaller increment or reduce the stimulation frequency in order to produce the desired heart rate response for the neural fulcrum zone 852-3.

FIG. 8C is a chart 880 illustrating mean heart rate response surfaces in conscious, normal dogs during 14 second periods of right cervical vagus VNS stimulation ON-time. The heart rate responses shown in z-axis represent the percentage heart rate change from the baseline heart rate at various sets of VNS parameters, with the pulse width the pulse width set at 250 μsec, the pulse amplitude ranging from 0 mA to 3.5 mA (provided by the x-axis) and the pulse frequency ranging from 2 Hz to 20 Hz (provided by the y-axis). Curve 890 roughly represents the range of stimulation amplitude and frequency parameters at which a null response (i.e., 0% heart rate change from baseline) is produced. This null response curve 890 is characterized by the opposition of functional responses (e.g., tachycardia and bradycardia) arising from afferent and efferent activation.

Titration Process

Several classes of implantable medical devices provide therapy using electrical current as a stimulation vehicle. When such a system stimulates certain organs or body structures like the vagus nerve, therapeutic levels of electrical stimulation are usually not well tolerated by patients without undergoing a process known as titration. Titration is a systematic method of slowly increasing, over time, stimulation parameters employed by an implanted device to deliver stimulation current until therapeutic levels become tolerated by the patient.

Figure 9:
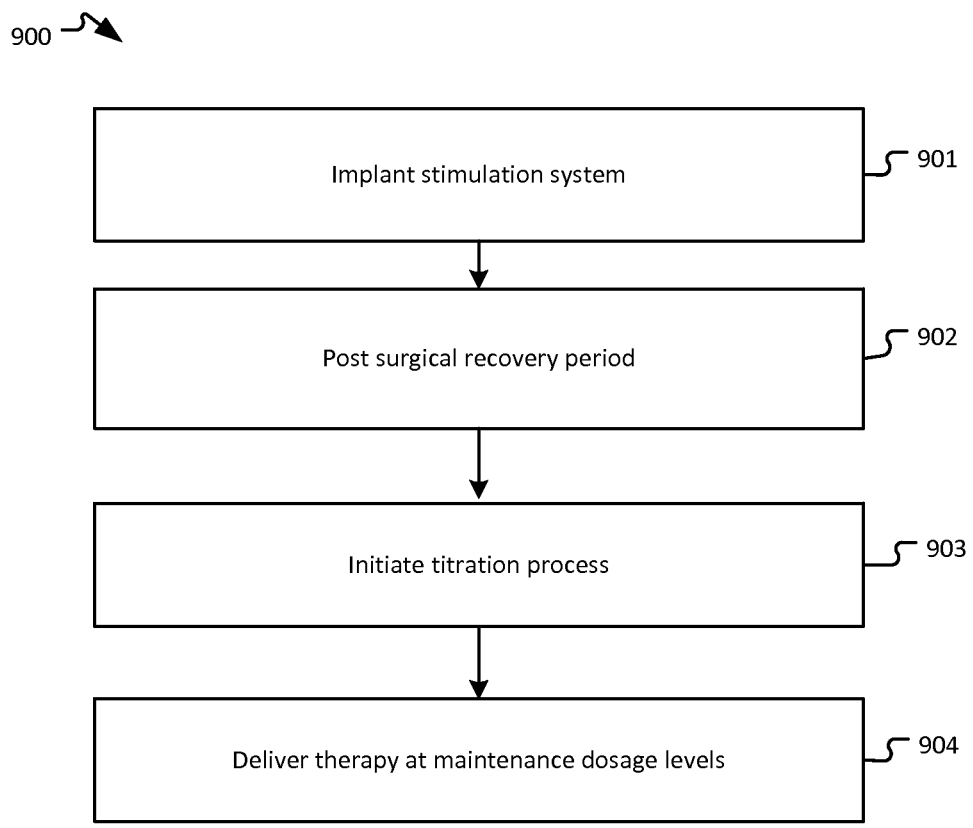
FIG. 9 illustrates a method for delivering vagus nerve stimulation therapy.

FIG. 9 is a flow diagram showing a method for delivering vagus nerve stimulation therapy, in accordance with embodiments of the present invention. A titration process is used to gradually increase the stimulation intensity to a desired therapeutic level. If the stimulation intensity is increased too quickly before the patient is fully accommodated to the stimulation signal, the patient may experience undesirable side effects, such as coughing, hoarseness, throat irritation, or expiratory reflex. The titration process gradually increases stimulation intensity within a tolerable level, and maintains that intensity for a period of time to permit the patient to adjust to each increase in intensity, thereby gradually increasing the patient's side effect tolerance zone boundary to so as to accommodate subsequent increases in intensity. The titration process continues until adequate adaptation is achieved. In embodiments, the titration process is automated and is executed by the implanted device without manual adjustment of the stimulation intensity by the subject or health care provider. As will be described in greater detail below, adequate adaptation is a composite threshold comprising one or more of the following: an acceptable side effect level, a target intensity level, and a target physiological response. In preferred embodiments, adequate adaption includes all three objectives: an acceptable side effect level, a target intensity level, and a target physiological response.

As described above, it may be desirable to minimize the amount of time required to complete the titration process so as to begin delivery of the stimulation at therapeutically desirable levels, particularly when the patient is being treated for an urgent condition such as CHF. In addition, it is desirable to utilize a maintenance dose intensity at the minimum level required to achieve the desired therapeutic effect. This can reduce power requirements for the neurostimulator and reduce patient discomfort.

It has been observed that a patient's side effect profile is more sensitive to the stimulation output current than to the other stimulation parameters, such as frequency, pulse width, and duty cycle. As a result, accommodation to the stimulation output current is a primary factor in completing the titration process. It has also been observed that if the other stimulation parameters are maintained at a level below the target levels, the output current can be increased to higher levels without eliciting undesirable side effects that would be result when the other parameters are at the target level. As a result, increasing the target output current while maintaining the other stimulation parameters (pulse width in particular) at reduced levels can result in a faster accommodation and shorter overall titration time than would be achieved by attempting to increase the output current while stimulating at the target pulse width.

In step 901, a stimulation system 11, including a neurostimulator 12, a nerve stimulation lead assembly 13, and a pair of electrodes 14, is implanted in the patient. In step 902, the patient undergoes an optional post-surgery recovery period, during which time the surgical incisions are allowed to heal and no VNS therapy occurs. This period may last, e.g., two weeks post surgery. In step 903, the stimulation therapy process is initiated. During this process, VNS therapy is titrated by adjusting one or more of the stimulation parameters, including output current, pulse width, signal frequency, and duty cycle, as will be described in greater detail below. Completion of the titration process determines the stimulation intensity to be used for subsequent maintenance doses delivered in step 904. These maintenance doses may be selected to provide the minimum stimulation intensity necessary to provide the desired therapeutic result.

Figure 10:
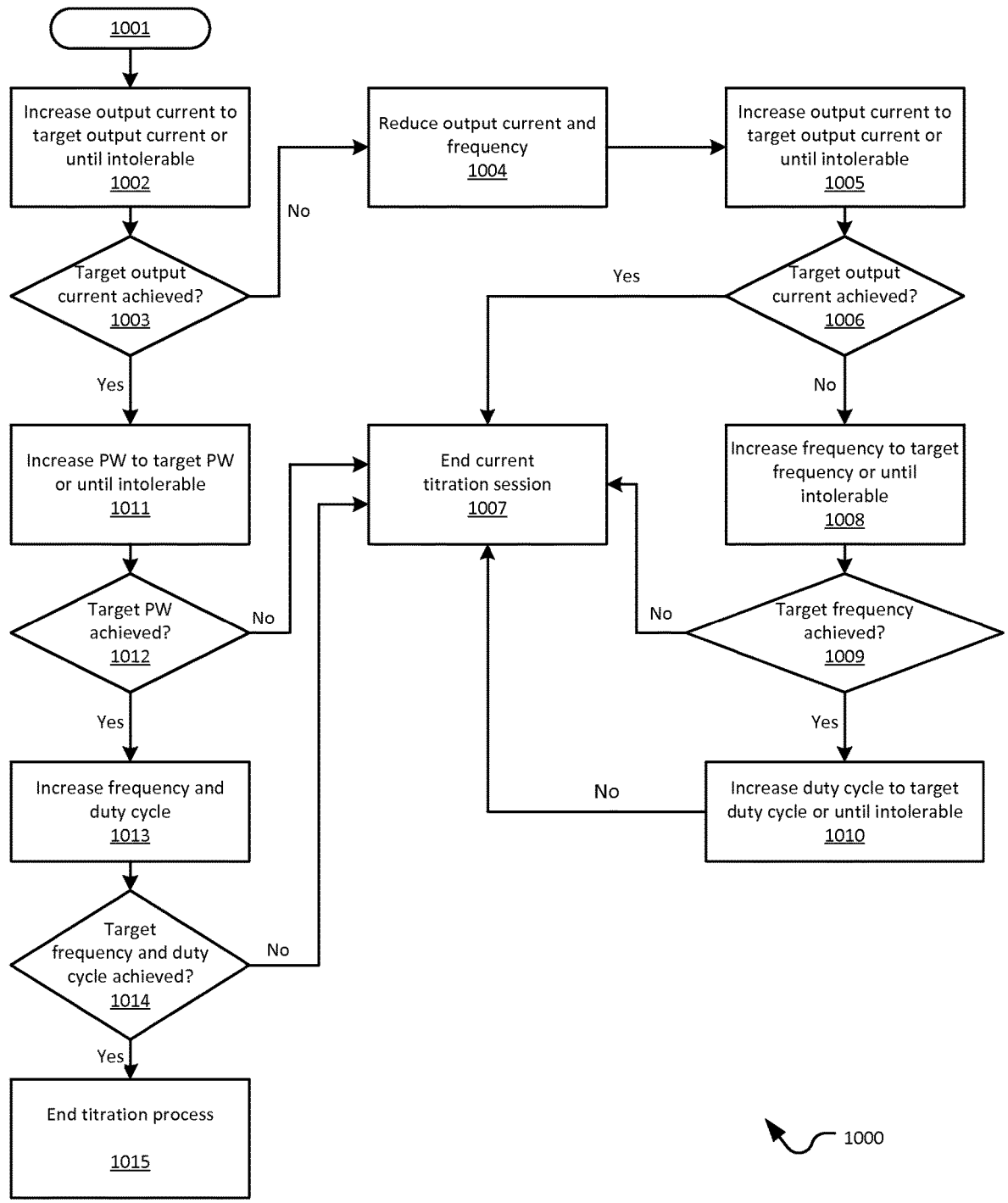
FIG. 10 illustrates a titration process in accordance with embodiments of the present invention.

FIG. 10 is a flow diagram illustrating a titration process 1000 in accordance with embodiments of the present invention. When first initiating the titration process, the neurostimulator 11 is configured to generate a stimulation signal having an initial stimulation parameter set. The initial parameter set may comprise an initial output current, an initial frequency, an initial pulse width, and an initial duty cycle. The various initial parameter settings may vary, but may be selected so that one or more of the parameters are set at levels below a predefined target parameter set level, such that the titration process is used to gradually increase the intensity parameters to achieve adequate adaptation. In some embodiments, the initial frequency is set at the target frequency level, while the initial output current, initial pulse width, and initial duty cycle are set below their respective target levels. In one embodiment, the target parameter set comprises a 10 Hz frequency, 250 μsec pulse width, a duty cycle of 14 sec ON and 1.1 minutes OFF, and an output current of between 1.5 mA-3.0 mA (e.g., 2.5 mA for right side stimulation and 3.0 mA for left side stimulation), and the initial parameter set comprises 10 Hz frequency, 130 μsec pulse width, a duty cycle of 14 sec ON and 1.1 minutes OFF, and an output current of between 0.25 mA-0.5 mA. In other embodiments, the target parameter set includes a 5 Hz frequency is used instead of a 10 Hz frequency.

In step 1001, the stimulation system delivers stimulation to the patient. If this is the first titration session, then the stimulation would be delivered with the initial stimulation parameter set described above. If this is a subsequent titration session, then the stimulation intensity would remain at the same level at the conclusion of the previous titration session.

In step 1002, the output current is gradually increased until the stimulation results in an intolerable side effect level, the target output current (e.g., 2.5 mA) is reached, or adequate adaptation is achieved. As described above, adequate adaptation is a composite threshold comprising one or more of the following: an acceptable side effect level, a target intensity level, and a target physiological response. In accordance with some embodiments, the target physiological response comprises a target heart rate change during stimulation. The patient's heart rate may be monitored using an implanted or external heart rate monitor, and the patient's heart rate during stimulation is compared to the patient's baseline heart rate to determine the extent of heart rate change. In accordance with some embodiments, the target heart rate change is a heart rate change of between 4% and 5%. If at any point during the titration process 1000 adequate adaptation is achieved, the titration process ends and the stimulation intensity which resulted in the adequate adaptation is used for ongoing maintenance dose therapy delivery.

The output current may be increased in any desired increment, but small increments, e.g., 0.1 mA or 0.25 mA, may be desirable so as to enable more precise adjustments. In some cases, the output current increments may be determined by the neurostimulator's maximum control capability. During the initial titration sessions, it is likely that the patient's side effect tolerance zone boundary will be reached well before the output current reaches the target level or adequate adaptation is achieved. At decision step 1003, if the target output current has not been achieved but the maximum tolerable side effects have been exceeded, the process proceeds to step 1004.

In step 1004, the output current is reduced one increment to bring the side effects within acceptable levels. In addition, the frequency is reduced. In embodiments in which the initial frequency was 10 Hz, in step 1004, the frequency may be reduced, e.g., to 5 Hz or 2 Hz.

Next, in step 1005, the output current is gradually increased again at the reduced frequency level until the stimulation results in an intolerable side effect level or the target output current (e.g., 2.5 mA) is reached. At decision step 1006, if the target output current has not been reached but the maximum tolerable side effects have been exceeded, the process proceeds to step 1007.

In step 1007, the titration session is concluded. The stimulation system may be programmed to continue delivering the stimulation signal at the last parameter settings achieved prior to conclusion of the titration session. After a period of time, another titration session may be initiated and the process returns to step 1001. This can be any period of time sufficient to permit the patient to adjust to the increased stimulation levels. This can be, for example, as little as approximately two or three days, approximately one to two weeks, approximately four to eight weeks, or any other desired period of time.

In some embodiments, the titration sessions are automatically initiated by the stimulation system or initiated by the patient without requiring any intervention by the health care provider. This can eliminate the need for the patient to schedule a subsequent visit to the health care provider, thereby potentially reducing the total amount of time needed for the titration process to complete. In these embodiments, the stimulation system may include a physiological monitor, e.g., an implanted heart rate sensor, that communicates with the stimulation system's control system to enable the control system to detect the patient's physiological response to the titration and automatically make adjustments to the titration processes described herein with reduced or no inputs from the patient or health care provider. The monitored signals can also enable the control system to detect when the target physiological response has been achieved and conclude the titration process. The stimulation system could in addition or alternatively include a patient control input to permit the patient to communicate to the control system that the acceptable side effect level has been exceeded. This control input may comprise an external control magnet that the patient can swipe over the implanted neurostimulator, or other internal or external communication device that the patient can use to provide an input to the control system. In these automatically initiated titration sessions, the stimulation system may be configured to wait a period of time after completing one session before initiating the next session. This period of time may be predetermined, e.g., two or three days, or programmable.

Returning to decision step 1006, if the target output current has not been reached but the maximum tolerable side effects have been exceeded, the process proceeds to step 1008. In step 1008, the output current is reduced one increment to restore an acceptable side effect condition, and the frequency is gradually increased until the stimulation results in an intolerable side effect level or the target frequency (e.g., 10 Hz) is reached. At decision step 1009, if the target frequency has not been reached but the maximum tolerable side effects have been exceeded, the frequency is reduced to restore an acceptable side effect level and the process proceeds to step 1007. Again, in step 1007, the current titration session is concluded and the stimulation system may be programmed to continue delivering the stimulation signal at the last parameter settings achieved prior to conclusion of the titration session.

At decision step 1009, if the target frequency has been reached before the maximum tolerable side effects have been exceeded, the duty cycle is gradually increased until the stimulation results in an intolerable side effect level or the target duty cycle (e.g., 14 sec ON and 1.1 min OFF) is reached, at which point the process proceeds to step 1007 and the titration session is concluded and ongoing stimulation delivered at the last intensity eliciting acceptable side effect levels.

Returning to decision step 1003, if the target output current has been achieved before the maximum tolerable side effects are exceeded, the process proceeds to step 1011. In step 1011, the pulse width is gradually increased until the stimulation results in an intolerable side effect level or the target pulse width (e.g., 250 μsec) is reached. In some embodiments, before step 1011, the output current is reduced (e.g., by up to 50%), and the pulse width may be increased in step 1011 at that reduced output current. After the target pulse width is achieved, the output current may be restored to the target output current. In other embodiments, the output current may be reduced (or may be retained at the reduced level established prior to step 1011, as described above), and the frequency and duty cycle are gradually increased in step 1013 at that reduced output current. This reduction in output current after achieving the target output current may enable the patient to maintain tolerability with increasing pulse width, frequency, and duty cycle in subsequent titration steps.

At decision step 1012, if the target pulse width has not been achieved before the maximum tolerable side effects have been exceeded, the pulse width is reduced to restore an acceptable side effect level and the process proceeds to step 1007. Again, in step 1007, the current titration session is concluded.

If at decision step 1012, the target pulse width has been achieved before the maximum tolerable side effects have been exceeded, the process proceeds to step 1013. In step 1013, the frequency and duty cycle are increased until the stimulation results in an intolerable side effect level or the target frequency and target duty cycle are reached. The frequency and duty cycle can be increased in step 1012 simultaneously, sequentially, or on an alternating basis.

At decision step 1014, if the target frequency and target duty cycle have not been achieved before the maximum tolerable side effects have been exceeded, the pulse width and/or frequency are reduced to restore an acceptable side effect level and the process continues to step 1007 and the titration session is concluded.

At decision step 1014, if the target pulse width and target frequency have been achieved before the maximum tolerable side effects have been exceeded, all of the stimulation parameters will have reached their target levels and the titration process concludes at step 1015. The stimulation therapy may proceed with the maintenance dose at the target stimulation levels.

In some embodiments, in step 1004, instead of reducing the frequency in order to facilitate increase of the output current, the pulse width may be reduced. For example, embodiments where the target pulse width is 250 μsec, the pulse width may be reduced, e.g., to 150 μsec or less. Then, the method proceeds to step 1005, in which the output current is gradually increased again at the reduced pulse width level until the stimulation results in an intolerable side effect level or the target output current (e.g., 2.5 mA) is reached.

Therapy can also be autonomously titrated by the neurostimulator 12 in which titration progressively occurs in a self-paced, self-monitored fashion. The progression of titration sessions may occur on an autonomous schedule or may be initiated upon receipt of an input from the patient. Ordinarily, the patient 10 is expected to visit his healthcare provider to have the stimulation parameters stored by the neurostimulator 12 in the recordable memory 29 reprogrammed using an external programmer. Alternatively, the neurostimulator 12 can be programmed to automatically titrate therapy by up titrating the VNS through periodic incremental increases using titration sessions as described above. The titration process 1000 will continue until the ultimate therapeutic goal is reached.

Following the titration period, therapeutic VNS, as parametrically defined by the maintenance dose operating mode, is delivered to at least one of the vagus nerves. The stimulation system 11 delivers electrical therapeutic stimulation to the cervical vagus nerve of a patient 10 in a manner that results in creation and propagation (in both afferent and efferent directions) of action potentials within neuronal fibers of either the left or right vagus nerve independent of cardiac cycle.

In a further embodiment, the sensed heart rate data can be used to analyze therapeutic efficacy and patient condition. For instance, statistics could be determined from the sensed heart rate, either onboard by the neurostimulator 12 or by an external device, such as a programming computer following telemetric data retrieval. The sensed heart rate data statistics can include determining a minimum heart rate over a stated time period, a maximum heart rate over a stated time period, an average heart rate over a stated time period, and a variability of heart rate over a stated period, where the stated period could be a minute, hour, day, week, month, or other selected time interval. Still other uses of the heart rate sensor 31 and the sensed heart rate data are possible.

FIG. 11A is a simplified block diagram of an implanted neurostimulation system 1100 in accordance with embodiments of the present invention. The implanted neurostimulation system 1100 comprises a control system 1102 comprising a processor programmed to operate the system 1100, a memory 1103, an optional physiological sensor 1104, and a stimulation subsystem 1106. The physiological sensor 1104 may be configured to monitor any of a variety of patient physiological signals and the stimulation subsystem 1106 may be configured to deliver a stimulation signal to the patient. In one example, the physiological sensor 1104 comprises an ECG sensor for monitoring heart rate and the stimulation subsystem 1106 comprises a neurostimulator 12 programmed to deliver ON-OFF cycles of stimulation to the patient's vagus nerve.

The control system 1102 is programmed to activate the neurostimulator 12 to deliver varying stimulation intensities to the patient and to monitor the physiological signals in response to those stimulation signals.

The external programmer 1107 shown in FIG. 11A may be utilized by a clinician or by the patient for communicating with the implanted system 1100 to adjust parameters, activate therapy, retrieve data collected by the system 1100 or provide other input to the system 1100. In some embodiments, the external programmer 1107 may be configured to program the implanted system 1100 with a prescribed time or window of time during which titration sessions may be initiated. This can be used to prevent a titration session from occurring at night when the patient's sleep is likely to be disturbed by the increase in stimulation intensity and resulting side effects.

Patient inputs to the implanted system 1100 may be provided in a variety of ways. The implanted system 1100 may include a patient input sensor 1105. As described above, a patient magnet 1130 may be used to provide external input to the system 1100. When the patient magnet 1130 is placed on the patient's chest in close proximity to the implanted system 1100, the patient input sensor 1105 will detect the presence of the magnetic field generated by the patient magnet 1130 and provide a control input to the control system 1102. The system 1100 may be programmed to receive patient inputs to set the time of day during which titration sessions are to be initiated.

In other embodiments, the patient input sensor 1105 may comprise a motion sensor, such as an accelerometer, which is configured to detect tapping on the surface of the patient's chest. The patient may use finger taps in one or more predetermined patterns to provide control inputs to the implanted system 1100. For example, when the motion sensor detects three rapid taps to the patient's chest, that may trigger an operation on the implanted system 1100 (e.g., to initiate a titration session). Alternatively, if the motion sensor detects a predetermined pattern of taps during a titration session, the implanted system 1100 will interpret those taps as a patient input indicating that the patient's tolerance zone boundary has been exceeded.

In other embodiments, the patient input sensor 1105 may comprise an acoustic transducer or other sensor configured to detect acoustic signals. The system 1100 may be programmed to interpret the detection of certain sounds as patient inputs. For example, the patient may utilize an electronic device, such as a smartphone or other portable audio device, to generate one or more predetermined sequences of tones. The system 1100 may be programmed to interpret each of these sequences of tones as a different patient input.

The titration of the stimulation signal delivery and the monitoring of the patient's physiological response (e.g., heart rate) may be advantageously implemented using control system in communication with both the stimulation subsystem 1106 and the physiological sensor 1104, such as by incorporating all of these components into a single implantable device. In accordance with other embodiments, the control system may be implemented in a separate implanted device or in an external programmer 1120 or other external device, as shown in FIG. 11B. The external programmer 1120 in FIG. 11B may be utilized by a clinician or by the patient for adjusting stimulation parameters. The external programmer 1120 is in wireless communication with the implanted medical device 1110, which includes the stimulation subsystem 1116. In the illustrated embodiment, the physiological sensor 1114 is incorporated into the implanted medical device 1110, but in other embodiments, the sensor 1114 may be incorporated into a separate implanted device, may be provided externally and in communication with the external programmer 1120, or may be provided as part of the external programmer 1120.

Managing Patient Discomfort Events

In other embodiments, the patient input sensor 1105 may be configured to detect when a patient is coughing, which can be interpreted by the system 1100 as an indication that the increased stimulation intensity exceeds the patient's tolerance zone boundary. The coughing could be detected by an accelerometer to detect movement of the patient's chest or lungs, an acoustic transducer to detect the sound of the patient's coughing, or both.

In various implementations, the patient input sensor 1105 may be a component housed within system 20 shown in FIG. 2A. The patient input sensor 1105 may one or more of an accelerometer, an acoustic sensor, an impedance sensor, a piezoelectric sensor, and a transthoracic impedance sensor. Further, the patient input sensor 1105 may detect a patient discomfort event such as a cough, a throat irritation, or a voice alteration of the patient.

An accelerometer may measure a displacement, which may be due to movement or sound. Acoustic energy may transmit through the body such that a cough, clearing of the throat, or a voice alteration may be detected by the accelerometer, but generally movement may be detected by the accelerometer. Various sounds may be detected and determinations of certain events occurring in the body may be made. Voice changes and coughs may transmit strong enough signals through the body that an accelerometer may be able to detect such events. The accelerometer may be applied with one or more filters and/or band pass settings to detect body posture (i.e., patient state). For example, the accelerometer may be used to determine if the patient is lying down verses sitting up or standing. The accelerometer may be positioned in the system 20 as shown in FIG. 2A which may be implanted in the patient's body for VNS therapy.

In an embodiment, the accelerometer may be positioned outside the system 20 but still in or around the patient's body and a signal may be transmitted from the accelerometer to the system 20 or an external device such as a programmer.

In an implementation, a method of detecting a voice alteration may include performing one or more signal processing operations on a sensed or detected voice or voice related signals. The voice or voice related signals may be acquired via an accelerometer, which may be configured to act as a microphone for the purposes of detecting voice or voice alterations. A Fast Fourier Transform (FFT) algorithm may observe modulation of the voice due to the stimulation treatment, which may result in a tremolo-like effect. This effect may be observable in the frequency domain.

In an embodiment, an acoustic sensor may be implemented instead of or in addition to other sensors such as an accelerometer. For example, a crystal-based sensor or other acoustic sensors may be tuned to detect acoustic signatures of various patient discomfort events described herein. In an embodiment, a transthoracic impedance sensor may be used to, for example, measure the change in the impedance across the lungs as a function of the lungs expanding in order to detect a patient discomfort event such as a cough, clearing of the throat, or voice alteration. In an implementation, a cough may create a transient signal imparted on such an impedance sensor by the lungs and may be detected by the transthoracic impedance sensor.

Figure 12:
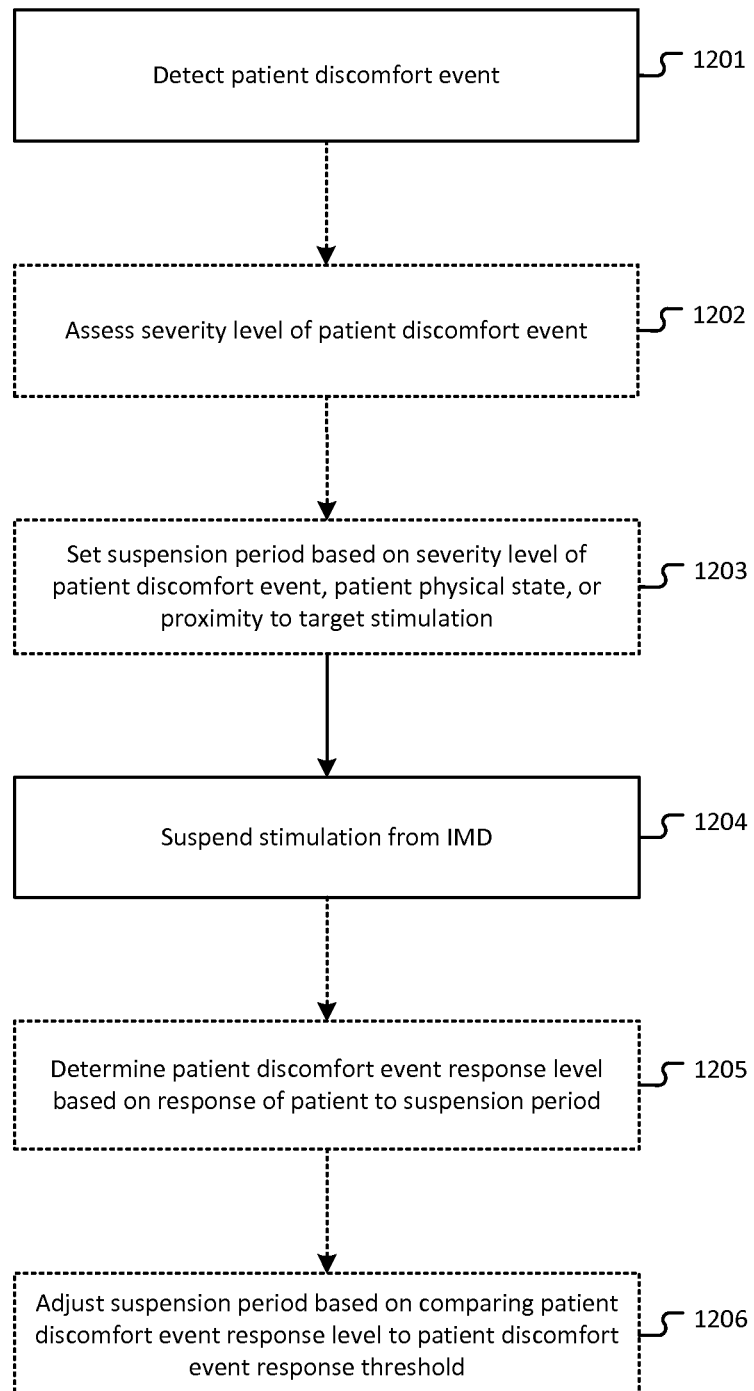
FIG. 12 illustrates a stimulation prevention process in accordance with embodiments of the present invention.

Referring now to FIG. 12, in an embodiment, when stimulation is initiated and increased, the system 20 may monitor the patient to detect a patient discomfort event via the patient input sensor 1105. For example, in step 1201, the system 20 may detect the patient discomfort event. In step 1204, in response to detecting the patient discomfort event, the system 20 may suspend the stimulation. The stimulation may be temporarily suspended for a set period of time that may progressively increase if such events are repeatedly detected. While various stimulation parameters may be adjusted in response to detecting a patient discomfort event side effect (e.g., reducing the stimulation intensity), it may be desirable in some situations to suspend the stimulation for a progressively increasing period of time to allow the patient to recover and adjust to the stimulation treatment, especially during the titration process.

Detecting the patient discomfort event may occur an ON cycle of the IMD (i.e., while stimulation is being administered). In this case, suspending the stimulation from the IMD may include transitioning the IMD to an OFF cycle (i.e., stimulation is no longer administered). In certain situations, detecting the patient discomfort event may occur during an OFF cycle of the IMD. In this case, suspending the stimulation from the IMD may include delaying initiation of an ON cycle of the IMD. The latter case may be applicable where the patient discomfort event is a voice or voice alteration, and stimulation is delayed while the patient is speaking. Once the patient finished speaking (as detected by one or more sensors as described herein), the stimulation may resume. Further, in an embodiment, suspending the stimulation from the IMD may include transitioning the IMD to an OFF cycle for the duration of a suspension period and transitioning the IMD to an ON cycle after the suspension period is over.

For example, in step 1205, the system 20 may determine a patient discomfort event response level based on a response of the patient to the suspension period. In an implementation, if the patient experiences another patient discomfort event immediately after the end of the suspension period, patient discomfort event response level may be low. If the patient does not experience another patient discomfort event until a relatively long time after the end of the suspension period, patient discomfort event response level may be high. In step 1206, the system 20 may adjust the suspension period based on comparing the patient discomfort event response level to a patient discomfort event response threshold. The patient discomfort event response threshold may be set by a clinician or may be a default setting may act as a mediator for how aggressively to increase or decrease the suspension period based on the patient's response. For example, if the patient discomfort event response level is very low or lower than the patient discomfort event response threshold, the suspension period may increase. If the patient discomfort event response level is very high or higher than the patient discomfort event response threshold, the suspension period may be decrease or it may be determined that suspension is no longer necessary.

Various methodologies may be used to intelligently suspend or delay stimulation during titration or subsequent treatment. For example, stimulation may be suspended for thirty seconds upon detecting a patient discomfort event (e.g., cough), and then suspended for forty-five seconds upon detecting another cough. In an embodiment, if the patient discomfort event is detected along with a particular patient state or movement (via, e.g., an accelerometer), it may also be determined that the patient is lying down as well as coughing. In this situation, for example, the suspension period or delay period for the stimulation may be shorter or longer based on knowledge that the patient is resting. In an implementation, based on the patient's level of activity or state, the techniques and features described herein may be used to suspend stimulation when a patient discomfort event is detected.

The suspension of stimulation/treatment may not always be a fixed-step approach. For example, in the beginning of the titration process (e.g., first few weeks) the suspension or delay of stimulation in response to detecting a patient discomfort event may be more aggressive or less aggressive between detections of patient discomfort events (e.g., coughs). During the early part of the titration process the patient may be more susceptible to experiencing patient discomfort events. In some situations, it may be desirable to have a shorter suspension period because certain patients may understand that there may be a higher degree of discomfort in the initial phases of titration and may be more willing to push through. For other patients, it may be more desirable to have initially longer suspension periods until the patient becomes acclimated to the treatment in order to make it easier for the patient to maintain a positive outlook. In step 1203, the system 20 may set (automatically, or, via, e.g., an external programmer) the suspension period based on a severity level of the patient discomfort event, a patient physical state (e.g., sleeping), or a proximity to a target stimulation.

The suspension period may be based on whether the patient is sleeping, lying down, awake, sitting, standing, and moving. For example, if the patient of sleeping or lying down, the suspension period may be longer in order to give the patient an opportunity to rest. Conversely, if the patient is standing or moving, the patient may be able to endure a shorter suspension period and receive more stimulation.

The suspension period may be based on a proximity of one or more parameters of the stimulation to one or more corresponding target stimulation parameters during the titration process. For example, the suspension period may be a function of how close the stimulation is to a target intensity or output being administered to the patient at the time of detecting a patient discomfort event. If the stimulation is close to the target intensity or output (i.e., near the end of the titration process), the suspension period may be shorter or longer depending on the goals set for titration and the particular patient. For example, if the stimulation is at the beginning of titration (e.g., 0.1 mA stimulation) and a cough is detected, the suspension period may be longer than if the stimulation is at the end of titration (e.g., 2.25 mA stimulation) and a cough is detected, where 2.5 mA may be the target intensity. This may be due to a break away point that some patients experience after getting used to the titration process where the patient may be able to handle rapidly increased stimulation intensities without feeling as many side effects as experienced earlier in the titration process. In this way, the clinician may tune the suspension timeframe on a patient by patient basis to manage patient discomfort events during titration.

In an embodiment, an intensity of a stimulation signal may be reduced on the fly during an ON cycle (e.g., by 50%) in response to detecting a patient discomfort event, however it may be more desirable to suspend the suspension entirely for the benefit of the patient's comfort and acclimation to the treatment.

In some situations, when titration is nearly over and the target stimulation intensity is nearly achieved, it may be less likely that certain patient discomfort events are detected. For example, if a patient is tolerating a relatively high level of stimulation intensity, patient discomfort events such as coughing may be less likely in the future because such a high level of intensity may not be ultimately necessary for the patient's treatment. In other words, the titration process may administer stimulation intensities higher than the patient receives after titration and during their VNS treatment regimen. However, other patient discomfort events such as voice alteration may be more likely to occur after the titration process and during the treatment regimen. In those cases the suspension period may be tuned around the detection of a voice alteration and such that when a voice is no longer being detected, the suspension period ends, and the stimulation is once again administered. In other words, the beginning of the suspension period and the end of the suspension period may both be triggered based on detection of a voice in the patient (e.g., via patient input sensor 1105). In this way, any social awkwardness that the patient may experience due to voice alteration may be minimized by suspending treatment while the patient is speaking. The voice alteration may or may not cause the patient substantial discomfort, however once the voice alteration is detected, suspension of treatment may be tuned around detecting the patient's voice such that the patient can speak more confidently.

In an implementation, detection of a patient discomfort event may be maximized for accuracy. Various criteria may be used to determine if a patient discomfort event is caused by a stimulation therapy or unrelated to the stimulation therapy. If the patient discomfort event is determined to be unrelated to the stimulation therapy, then stimulation most likely will not need to be suspended in response. For example, when stimulation is administered, it may be expected that a patient discomfort event, if caused by the stimulation, may occur within a short window of time after the stimulation is initiated, or shortly after the beginning of an ON cycle. If a patient discomfort event (e.g., a cough) is detected after initiation of an OFF cycle (e.g., 30 seconds after, for example), it may be determined that the patient discomfort event did not occur due to the stimulation. In this way faults and false positives for patient discomfort event detection may be eliminated and these events can be attributed to other causes besides stimulation, such as sickness, common cold, abnormal swallowing, etc.

In an implementation, the window of time after the beginning of an ON cycle for which a positive or true patient discomfort event may be detected may be referred to as a qualification window and may be adjusted on a patient by patient or treatment by treatment basis. The qualification window may vary during the course of one patient's stimulation therapy regimen. For example, there may typically be about a two-second ramp up to an intended stimulation intensity at certain stimulation frequencies, and by the end of the ramp-up, a patient discomfort event may occur. In some situations, for, example one or two coughs may be detected immediately after the ramp-up and then for the remainder of the ON cycle coughing may no longer be detected. At greater intensities, a cough may start almost immediately at the end of the ramp-up and may persist throughout the entire ON cycle, but then may stop at the end of the ON cycle. In other situations, the false positives may be determined based on having detected a series of coughs during an ON Cycle which persist into an OFF cycle for a sufficient length of time such that it may be assumed that the patient has a cold or other irritant. Stimulation therapy in this situation may not be suspended because it has been determined that the cough or other patient event is not caused by the stimulation itself, but rather a different medical issue. The qualification window may be determined by a physician or automatically by the system 20 during a training session (as discussed below). Results of the evaluation during the training session, which may have been obtained while determining the qualification window or other parameters, may be logged or recorded to assist the physician or the system 20 with a root cause analysis (i.e., to determine whether the patient discomfort event is related to the stimulation or can be attributed to another cause). The logging feature may be automated via the pulse generator. Logging the outcome of an evaluation may be good practice because the physician may gain additional insight on the interaction of the system and the patient.

In an embodiment, patient discomfort events may rarely be detected during an OFF cycle. Further, at lower stimulation intensities, patient discomfort events may be detected immediately upon administration of the stimulation but may not persist throughout the entire ON cycle. In this way, various factors related to the timing of a patient discomfort event in relation to the starting and stopping of the stimulation may be used to set the qualification window.

In an implementation, the number of ON cycles analyzed before a true or positive patient discomfort event is determined to have occurred may vary. For example, in some situations, an event (e.g., cough, voice alteration) detected in a single ON cycle may not qualify as a true or positive patient discomfort event. Stimulation may be administered for a single ON cycle and detect a mild cough which may not qualify as a true or positive patient discomfort event. In this situation, another ON cycle may be administered to determine whether another cough is detected, or two additional ON cycles may be administered to verify that the cough is persistent enough to be characterized as a true or positive patient discomfort event.

In an embodiment, increases or decreases in the suspension period for the stimulation may not be linear or uniform. For example, the step size of the increase or decrease of the suspension period may progress linearly or nonlinearly as the suspension period is tuned based on patient response. As a result, the suspension time for the stimulation may become longer (if, e.g., multiple or severe patient discomfort events are experienced) or possibly shorter (if, e.g., fewer or less severe patient discomfort events are experienced) and the corresponding suspension period changes may not move along a linear progression. Further, various patient states as discussed above may factor into the step sizes for increasing or decreasing the suspension period.

Managing patient discomfort may also include adjusting the burst of a stimulation signal after suspending stimulation in response to detecting the patient discomfort event. Instead of linearly ramping up (or down) the intensity of the stimulation signal until the desired intensity is reached, a first section of the ramp up may be administered at, for example, half the burst or a quarter of the burst and the burst may be gradually increased over the course of the ramp up. Several different step sizes may be administered within the burst such that the patient may potentially accommodate stimulation more easily during the burst or ramp up itself.

For example, a patient may suffer a patient discomfort event (e.g., a cough) in response to a stimulation increase from 1.25 mA to 1.5 mA. The stimulation may be suspended as described here, however when the stimulation is resumed the burst level of the stimulation signal may be adjusted accordingly. In an implementation, the stimulation may resume at 1.25 mA for 10 seconds, and then burst to 1.375 mA for 10 seconds, and then finally burst to 1.5 mA. As a result, a cough response may be detected during the first mini-burst to 1.375 mA and the stimulation may once again be suspended. If no cough response is detected during the first mini-burst, the second mini-burst may proceed and the stimulation signal may increase to an intensity of 1.5 mA.

In step 1202, in an embodiment, a severity of a patient discomfort event or a series of patient discomfort events may be assessed. For example, patient input sensor 1105 (e.g., an accelerometer or acoustic sensor) may transmit a value to electronic circuitry 22 of system 10. The value may correspond to, or may be used to determine, the severity of the patient discomfort event. For example, a low value or weak detection from the patient input sensor 1105 may correspond to a clearing of the throat, or a low intensity cough. A high value or strong detection from the patient input sensor 1105 may correspond to a hard cough or a hacking cough (i.e., a higher intensity side effect). As a result, a longer suspension period may be set for suspending the stimulation in response to, e.g., a hacking cough and a shorter suspension period may be set for suspending the stimulation in response to e.g., a clearing of the throat.

In an embodiment, the severity of the patient discomfort event may be quantified (e.g., as a value) and compared to a patient discomfort event threshold. If the quantified value of the patient discomfort event (reflecting the severity of a cough) is greater than the patient discomfort event threshold, stimulation treatment may be suspended for a suspension period, which may be set as described herein. In an implementation, for a high magnitude cough (severe), suspension may occur almost immediately because a violent patient discomfort event was detected (e.g., by accelerometer) as compared to the patient discomfort event threshold. In another implementation, a mild cough which occurs during a ramp-up of an ON cycle may not cross the patient discomfort event threshold until the mild cough occurs during multiple ON cycles.

The severity of the patient discomfort event may be determined by a program or an algorithm using the value received from patient input sensor 1105. For example, a value received from an accelerometer or acoustic sensor may be used to determine the duration of a cough. The cough may have been fast or may have caused a large deflection in acceleration and a very rapid and high magnitude acceleration may have been detected. In another situation, a mild cough may cause a smaller magnitude acceleration over a longer period. Various permutations of acceleration magnitude and acceleration period may be detected and used to quantify the severity of the cough. For example, the severity of the cough may not be based solely on the intensity of a single cough, but may also be based on the number and persistence of coughs (e.g., time length of a series of coughs) that occur in series. The severity of the patient discomfort event may also be determined during the titration process and a calibration method described below may be implemented during a training mode for the patient.

Interactive Training Sessions (Training Mode)

Various methods are described herein for titrating stimulation by gradually increasing stimulation intensity until the patient's tolerance zone boundary is reached or exceeded. In accordance with embodiments of the present invention, systems and methods are provided for performing interactive training sessions in clinic for patients about to undergo titration on an ambulatory basis. The methods permit clinicians to create a series of stimulation intensities (ranging from un-noticeable to noticeable but tolerable to intolerable), the patient's response to each stimulation, and the implanted device's response to patient inputs. A training session may be administered to determine what patient discomfort events are intolerable enough such that stimulation should suspended for a set suspension period.

The implanted medical device 1100 may be used in conjunction with an external clinician programmer 1107 and patient input device (e.g., patient magnet 1130 or wireless-communications-enabled patient control device), to perform the titration processes on an ambulatory basis as described above, but is also programmed to execute in a training mode. This training mode may be initiated by the clinician using the clinician programmer 1107 while the patient is physically in the clinic for treatment and training. The training mode may be similar to the titration sessions described above, except that the increasing stimulation is initiated by the clinician using the programmer 1107 or automatically on an accelerated schedule. When the stimulation intensity reaches the patient's tolerance zone boundary, the patient can use any of the herein described methods for providing a patient input to the device 1100 to indicate that the tolerance zone boundary has been reached. When in training mode, the device 1100 may also transmit to the clinician programmer 1107 information regarding the stimulation being delivered. The programmer 1107 may include a display which permits the clinician to observe the increasing intensity and receive a report of the intensity level that elicited the patient input indicating that the tolerance zone boundary was reached. The display on the programmer 1107 may also be used to display feedback or instructions to the patient.

The clinician may run the training mode multiple times so that the patient may become proficient at recognizing stimulation levels that are noticeable but tolerable, and distinguishing those tolerable levels from the truly intolerable stimulation levels. This can also provide training for the patient in the proper use of the patient input device. In some embodiments, the programmer 1107 may be used to select the stimulation parameter to be increased (e.g., output current, frequency, pulse width, or duty cycle), so that the patient and clinician can observe the different responses that may be elicited depending on the parameter being adjusted. In some embodiments, the programmer 1107 may be configured to pause the titration algorithm to hold the stimulation at a single level. This may be useful for facilitating a tolerance zone assessment by providing the patient additional time to experience the stimulation. The programmer 1107 may also be used to terminate the training mode and return the device 1100 to its normal ambulatory mode, during which the desired ambulatory titration process may be performed.

The training mode may also comprise an algorithm that sequences stimulation changes based on the training mode parameters programmed by the clinician. Stimulation may be altered on a highly accelerated time scale in order to move the patient from tolerable to noticeable-but-tolerable to intolerable stimulation levels within the normal office follow-up period. This accelerated time scale may be, for example, five, ten or fifteen minutes for all training. This is in contrast to the ambulatory mode titration process that seeks to advance therapy levels without the patient exceeding the tolerance-zone boundary. Having the patient experience all three tolerance phases in a single clinic visit can provide valuable patient training, resulting in accelerated adaptation speed.

The system 1100 may be programmed with an autonomous monitor to ensure that the training mode terminates automatically after a certain period has elapsed, even in the absence of a termination input from the clinician programmer. For example, the system 1100 may be programmed to automatically time-out and terminate the training mode 24 hours after initiation. After this automatic time-out, the system 1100 may automatically initiate the ambulatory mode.

As discussed above, severity of patient discomfort events may be assessed during the titration process and a calibration process for such assessment may be implemented during the training mode for the patient. The calibration process may be used to calibrate sensors and the system 20 to determine what is and is not a patient discomfort event that requires a suspension response and to determine the severity of the patent discomfort event. The result of the calibration process is that the sensors and system 20 may recognize, upon receiving values from one or more sensors, whether or not a patient discomfort event has occurred during stimulation treatment and whether or not suspension of stimulation is required in response.

Referring now to FIG. 13, a calibration process 1300 is shown and may be part of a training mode initiated during the titration process. The calibration process may be run with a patient and parameters may be set for the system 20 to function autonomously in managing patient discomfort events. In step 1301, as part of the calibration process, a clinician may administer or increase a stimulation to elicit a patient discomfort event (e.g., a hacking cough). The training mode may also administer the stimulation automatically via an external programmer or electronic instructions run by the system 20 during the calibration process. In step 1302, the patient may be prompted to produce a patient discomfort event. The elicited patient discomfort event may be compared (e.g., automatically by the system 20 or the external programmer, or manually by the clinician) to, for example, a normal cough or a normal speaking voice, in order to determine any distinction between the two. In step 1303, the system 20 may receive an indication of the patient discomfort event (e.g., via an accelerometer, acoustic sensor, or other sensor described herein).

The training mode may be used to make the patient more comfortable or acclimate the patient with the stimulation intensity they are likely to experience during their treatment. In some situations, a patient discomfort event may not last through the training or may cease to appear after the training. In other situations, a patient discomfort event may continue and it may be determined that stimulation needs to be suspended. In an embodiment, an external programmer may be used by the clinician to identify when the patient suffers from a patient discomfort event (e.g., a hacking cough). The clinician may provide an input to the programmer to indicate that a patient discomfort event occurred, and the programmer or the system 20 may record the stimulation circumstances under which the patient discomfort event occurred, including any sensor (e.g., accelerometer) response, such that the system 20 can identify a similar patient discomfort event in the future. In this way, in step 1304, the system 20 may calibrate detection of the patient discomfort event. As described herein, calibrating detection of the patient discomfort event may be performed automatically or manually via a programmer.

While the training mode and calibration method may run automatically via the system 20 and/or the external programmer, a manual programming session may be used in an embodiment at the beginning of the training mode to set initial parameters (e.g., sensor parameters, suspension parameters, ramp-up parameters, etc.) and identify the first patient discomfort events.

For example, during the training mode and while proceeding through the calibration process, a violent cough may be detected. The system 20 may be trained to have a faster response time for suspending the stimulation after violent cough as compared to a shorter response time for a less severe cough. For a violent cough or series of coughs, the onset of the cough may register only slightly with the sensor (e.g., accelerometer) until the cough peaks. The cough may then register considerably with the sensor. In other words, the amplitude detected by the sensor may be greater for a hacking cough than a soft cough, and the severity of the cough can be characterized and learned by the system 20 during the training. Other factors that may be used to train the system to detect the severity of the patient discomfort event may be magnitude, duration, and timing relative to the stimulation. As a result, based on the onset characteristics of, for example, a cough (e.g., from when the cough starts until it reaches its peak), the response time for suspension of stimulation may be shorter or longer, i.e., the response time for suspension is shorter for the more violent coughs than the softer coughs.

As a result, the system with stimulation suspension may enable patients to experience stimulation levels (usually following a stimulation increase) that may at first be unacceptable. Patients may also learn how to effectively deal with the intolerance through the use of the external patient input device or automatic or manual calibration processes and training mode described herein. Clinicians can learn how individual patients react to various stimulation levels and the patients' cognitive ability to deal with unacceptable stimulation autonomously. Clinicians may also gain a sense of stimulation increases that an individual patient can tolerate and suspend stimulation accordingly. Suspension of stimulation may be done automatically upon detecting patient discomfort events and completing the calibration process described herein. Detection of patient discomfort events may be calibrated in the training mode.

While the invention has been particularly shown and described as referenced to the embodiments thereof, those skilled in the art will understand that the foregoing and other changes in form and detail may be made therein without departing from the spirit and scope. For example, in various embodiments described above, the stimulation is applied to the vagus nerve. Alternatively, spinal cord stimulation (SCS) may be used in place of or in addition to vagus nerve stimulation for the above-described therapies. SCS may utilize stimulating electrodes implanted in the epidural space, an electrical pulse generator implanted in the lower abdominal area or gluteal region, and conducting wires coupling the stimulating electrodes to the generator.

What is claimed is:

1. A method of suspending stimulation from an implantable medical device (IMD) in response to detecting a patient discomfort event, said method comprising:
   detecting the patient discomfort event, the patient discomfort event comprising at least one of a cough, a throat irritation, or a voice alteration;
   determining a severity of the patient discomfort event, wherein determining the severity of the patient discomfort event comprises differentiating between the at least one of the cough, the throat irritation, or the voice alteration having a first intensity corresponding to a first severity value or a second intensity corresponding to a second severity value;
   determining a suspension period based on the severity of the patient discomfort event; and
   in response to detecting the patient discomfort event, suspending the stimulation from the IMD for a duration of the suspension period.

2. The method according to claim 1, wherein:
   the detecting the patient discomfort event further comprises detecting the patient discomfort event during an ON cycle of the IMD; and
   the suspending the stimulation from the IMD comprises transitioning the IMD to an OFF cycle.

3. The method according to claim 1, wherein:
   the detecting the patient discomfort event further comprises detecting the patient discomfort event during an OFF cycle of the IMD; and
   the suspending the stimulation from the IMD comprises delaying initiation of an ON cycle of the IMD.

4. The method according to claim 1, wherein:
   the detecting the patient discomfort event comprises detecting the patient discomfort event via at least one of: an accelerometer, an acoustic sensor, an impedance sensor, a piezoelectric sensor, or a transthoracic impedance sensor.

5. The method of claim 1, further comprising:
   setting the suspension period based on a proximity of one or more parameters of the stimulation to one or more corresponding target stimulation parameters during a titration process.

6. The method of claim 1, wherein:
   the suspension period is based on a patient physical state.

7. The method of claim 6, wherein:
   the patient physical state is selected from at least one of: sleeping, lying down, awake, sitting, standing, or moving.

8. The method according to claim 1, further comprising:
   determining a patient discomfort event response level based on a response of a patient to the suspension period; and
   adjusting the suspension period based on comparing the patient discomfort event response level to a patient discomfort event response threshold.

9. The method according to claim 8, wherein:
   the determining the patient discomfort event response level comprises detecting one or more additional patient discomfort events.

10. The method according to claim 8, wherein:
    the adjusting the suspension period comprises nonlinearly increasing or decreasing the suspension period.

11. The method according to claim 1, wherein the patient reaction having the first intensity is a clearing of a throat of the patient or a low intensity cough and the patient reaction having the second intensity is a hard cough or a hacking cough.

12. An implantable medical device (IMD) comprising:
a sensor;
a processor coupled to the sensor; and
a memory operably coupled to the processor and comprising instructions that, when executed by the processor, cause the processor to:
detect a patient discomfort event via the sensor, the patient discomfort event comprising at least one of a cough, a throat irritation, or a voice alteration;
determine a severity of the patient discomfort event, wherein determining the severity of the patient discomfort event comprises differentiating, using data received by the processor from the sensor, between the at least one of the cough, the throat irritation, or the voice alteration having a first intensity corresponding to a first severity value or a second intensity corresponding to a second severity value;
determine a suspension period based on the severity of the patient discomfort event; and
in response to detecting the patient discomfort event, suspend the stimulation from the IMD for a duration of the suspension period.

13. The device according to claim 12, wherein the sensor is at least one of: an accelerometer, an acoustic sensor, an impedance sensor, a piezoelectric sensor, or a transthoracic impedance sensor.

14. The device according to claim 12, wherein the processor is further configured to:
determine a patient discomfort event response level based on a response of a patient to the suspension period; and
adjust the suspension period based on comparing the patient discomfort event response level to a patient discomfort event response threshold.

15. A method of suspending stimulation from an implantable medical device (IMD) in response to detecting a patient discomfort event, said method comprising:
detecting the patient discomfort event via a sensor in the IMD, wherein the patient discomfort event comprises at least one of a cough, a throat irritation, or a voice alteration and detecting the patient discomfort event comprises differentiating between the at least one of the cough, the throat irritation, or the voice alteration corresponding to a first discomfort event value or a second discomfort event value;
assessing a severity level of the patient discomfort event based on the patient discomfort event value received from the sensor;
in response to detecting the patient discomfort event, suspending the stimulation from the IMD by:
transitioning the IMD to an OFF cycle for the duration of a suspension period; and
transitioning the IMD to an ON cycle after the suspension period; and
wherein the suspension period is based on the severity level of the patient discomfort event and a patient physical state.

16. The method according to claim 15, wherein:
the sensor is selected from the group consisting of: an accelerometer, an acoustic sensor, an impedance sensor, a piezoelectric sensor, or a transthoracic impedance sensor.

17. The method according to claim 15, wherein:
the patient physical state is at least one of: sleeping, lying down, awake, sitting, standing, or moving.

18. The method according to claim 15, wherein:
the suspension period is longer based on the patient physical state being at least one of sleeping or lying down as compared to the physical state being at least one of awake, sitting, or standing.

* * * * *